US006506750B1

(12) United States Patent
Ducoux et al.

(10) Patent No.: US 6,506,750 B1
(45) Date of Patent: Jan. 14, 2003

(54) MORPHOLINE DERIVATIVES, METHOD FOR THE PRODUCTION THEREOF AND PHARMACEUTICAL PREPARATIONS CONTAINING SAID DERIVATIVES

(75) Inventors: Jean-Philippe Ducoux, Combaillaux (FR); Xavier Emonds-Alt, Combaillaux (FR); Patrick Gueule, Teyran (FR); Vincenzo Proietto, Saint Georges D'orques (IT)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/937,279
(22) PCT Filed: Mar. 21, 2000
(86) PCT No.: PCT/FR00/00695
§ 371 (c)(1),
(2), (4) Date: Sep. 24, 2001
(87) PCT Pub. No.: WO00/58292
PCT Pub. Date: Oct. 5, 2000

(30) Foreign Application Priority Data

Mar. 25, 1999 (FR) ............................................ 99 03854

(51) Int. Cl.⁷ ................. C07D 265/30; A61K 31/5375; A61P 11/00
(52) U.S. Cl. ................. 514/235.8; 514/237.5; 514/252.13; 544/121; 544/359
(58) Field of Search ................. 544/121, 359; 514/235.8, 252.13, 237.5

(56) References Cited

U.S. PATENT DOCUMENTS 5,780,466 A * 7/1998 Emonds-Alt et al. .... 514/228.2
5,977,359 A   11/1999 Emonds-Alt

FOREIGN PATENT DOCUMENTS

| EP | 0 776 893 | 6/1997 |
| WO | 96/23787 | 8/1996 |
| WO | 99/28307 | 6/1999 |

OTHER PUBLICATIONS

Derwent Abstract 1999–198980.
Chemical Abstract 218281.
Derwent Abstract 1999–371085.

\* cited by examiner

*Primary Examiner*—Joseph K. McKane
*Assistant Examiner*—Kamal Saeed
(74) *Attorney, Agent, or Firm*—Paul E. Dupont; Michael D. Alexander

(57) ABSTRACT

N-(phenylacetyl)morpholine derivatives useful as NK1 receptor antagonists, a process for the preparation thereof, and pharmaceutical compositions containing them as active principle.

37 Claims, No Drawings

MORPHOLINE DERIVATIVES, METHOD FOR THE PRODUCTION THEREOF AND PHARMACEUTICAL PREPARATIONS CONTAINING SAID DERIVATIVES

This application is a 371 of PCT/FR00/00695 filed Mar. 21, 2000.

The present invention relates to novel morpholine derivatives, to a process for preparing them and to pharmaceutical compositions containing them as active principle.

More particularly, the present invention relates to novel morpholine derivatives for therapeutic use in pathological phenomena involving the tachykinin system, such as, in a non-limiting manner: pain (L. Urban et al., TINS, 1994, 17, 432–438; L. Seguin et al., Pain, 1995, 61, 325–343; S. H. Buck, 1994, The Tachykinin Receptors, Humana Press, Totowa, N.J.), allergy and inflammation (S. H. Buck, 1994, The Tachykinin Receptors, Humana Press, Totowa, N.J.), gastrointestinal disorders (P. Holzer and U. Holzer-Petsche, Pharmacol. Ther., 1997, 73, 173–217 and 219–263), respiratory disorders (J. Mizrahi et al., Pharmacology, 1982, 25, 39–50; C. Advenier et al., Eur. Respir. J., 1997, 10, 1892–1906; C. Advenier and X. Emonds-Alt, Pulmonary Pharmacol., 1996, 9, 329–333), urinary disorders (S. H. Buck, 1994, The Tachykinin Receptors, Humana Press, Totowa, N.J.; C. A. Maggi, Progress in Neurobiology, 1995, 45, 1–98), neurological disorders and neuropsychiatric disorders (C. A. Maggi et al., J. Autonomic Pharmacol., 1993, 13, 23–93; M. Otsuka and K. Yoshioka, Physiol. Rev. 1993, 73, 229–308).

Many research studies have been carried out in recent years on tachykinins and their receptors. Tachykinins are distributed both in the central nervous system and in the peripheral nervous system. The tachykinin receptors have been recognized and are classified into three types: $NK_1$, $NK_2$ and $NK_3$. Substance P (SP) is the endogenous ligand of the $NK_1$ receptors, neurokinin A ($NK_A$) is that of the $NK_2$ receptors and neurokinin B ($NK_B$) is that of the $NK_3$ receptors.

The $NK_1$, $NK_2$ and $NK_3$ receptors have been demonstrated in various species.

A review by C. A. Maggi et al. (J. Autonomic Pharmacol., 1993, 13, 23–93) and a review by D. Regoli et al. (Pharmacol. Rev., 1994, 46, 551–599) discuss tachykinin receptors and their antagonists and present the pharmacological studies and the applications in human therapy.

Many patents and patent applications describe compounds that are active on tachykinin receptors. Thus, International Application WO 96/23787 relates to the compounds of formula:

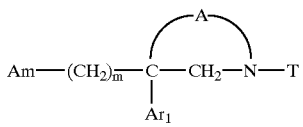

(A)

in which in particular:

A may represent the bivalent radical —O—$CH_2$—$CH_2$—;

Am, m, $Ar_1$ and T have different values.

Patent application EP-A-0 776 893 relates to the compounds of formula:

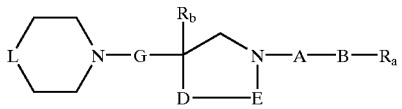

(B)

in which in particular

D—E may represent a bivalent radical —O—$CH_2$—$CH_2$—;

L, G, E, A, B, $R_a$ and $R_b$ have different values.

Novel compounds have now been found which have a very strong affinity and great selectivity for the human $NK_1$ receptors of substance P and which are antagonists of the said receptors.

Furthermore, the compounds according to the present invention have good bioavailability when they are administered orally.

These compounds can be used to prepare medicinal products that are useful in the treatment of any pathology in which substance P and the $NK_1$ receptors are involved, in particular in the treatment of pathologies of the respiratory, gastrointestinal, urinary, immune, cardiovascular and central nervous systems as well as in the treatment of pain, migraine, inflammations, nausea and vomiting, and skin diseases.

Thus, according to one of its aspects, a subject of the present invention is compounds of formula:

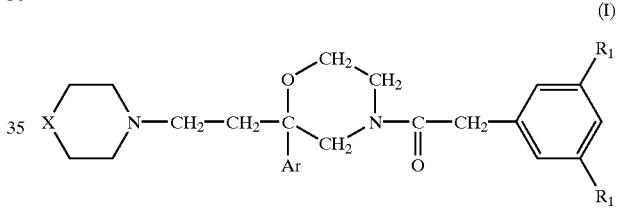

(I)

in which:

Ar represents a phenyl monosubstituted or disubstituted with a halogen atom; a ($C_1$–$C_3$)alkyl;

X represents a group;

a group;

$R_1$ represents a chlorine atom, a bromine atom, a ($C_1$–$C_3$) alkyl or a trifluoromethyl;

$R_2$ represents a ($C_1$–$C_6$)alkyl; a ($C_3$–$C_6$)cycloalkyl; a group —$CR_4R_5CONR_6R_7$;

$R_3$ represents a group —$CR_4R_5CONR_6R_7$;

$R_4$ and $R_5$ represent the same radical chosen from a methyl, an ethyl, an n-propyl or an n-butyl;

or alternatively $R_4$ and $R_5$, together with the carbon atom to which they are attached, constitute a ($C_3$–$C_6$) cycloalkyl;

$R_6$ and $R_7$ each independently represent a hydrogen; a $(C_1-C_3)$ alkyl;

or alternatively $R_6$ and $R_7$, together with the nitrogen atom to which they are attached, constitute a heterocyclic radical chosen from 1-azetidinyl, 1-pyrrolidinyl, 1-piperidinyl, 4-morpholinyl, 4-thiomorpholinyl or perhydro-1-azepinyl;

as well as the possible salts thereof with inorganic or organic acids, the solvates thereof and/or the hydrates thereof.

The compounds of formula (I) according to the invention comprise both optically pure isomers and mixtures thereof in any proportion.

Salts of the compounds of formula (I) can be formed. These salts comprise both those with inorganic or organic acids which allow a suitable separation or crystallization of the compounds of formula (I), such as picric acid or oxalic acid or an optically active acid, for example a mandelic or camphorsulphonic acid, and those which form pharmaceutically acceptable salts, such as the hydrochloride, hydrobromide, sulphate, hydrogen sulphate, dihydrogen phosphate, methanesulphonate, methyl sulphate, oxalate, maleate, fumarate, succinate, 2-naphthalenesulphonate, gluconate, citrate, isethionate, benzenesulphonate or para-toluenesulphonate.

Halogen atom is understood to mean a chlorine, bromine, fluorine or iodine atom.

In the present description, the alkyl groups are straight or branched.

According to the present invention, the compounds of formula (I) in which Ar represents a 3,4-dichlorophenyl are preferred.

According to the present invention, the preferred compounds of formula (I) are those in which the substituents $R_1$ represent a chlorine atom, a methyl, an ethyl, an isopropyl or a trifluoromethyl.

According to the present invention, the preferred compounds of formula (I) are those in which X represents a group

in which $R_2$ represents a $(C_1-C_6)$alkyl or a $(C_3-C_6)$cycloalkyl. Particularly, the preferred compounds are those in which $R_2$ represents a cyclopentyl or a cyclohexyl.

According to the present invention, the preferred compounds of formula (I) are those in which X represents a group

in which $R_2$ represents a group —$CR_4R_5CONR_6R_7$.

In this case, the preferred compounds are those in which $R_4$ and $R_5$ each represent a methyl or alternatively, together with the carbon atom to which they are attached, constitute a cyclohexyl. Particularly, the compounds which are also preferred are those in which $R_6$ and $R_7$ are similar and represent hydrogen or a methyl.

According to the present invention, the preferred compounds of formula (I) are those in which X represents a group

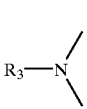

in which $R_3$ represents a group —$CR_4R_5CONR_6R_7$.

In this case, the preferred compounds are those in which $R_4$ and $R_5$ each represent a methyl or alternatively, together with the carbon atom to which they are attached, constitute a cyclopropyl or a cyclohexyl. Particularly, the compounds which are also preferred are those in which $R_6$ and $R_7$ are similar and represent hydrogen or a methyl.

According to the present invention, the compounds which are preferred are those of formula:

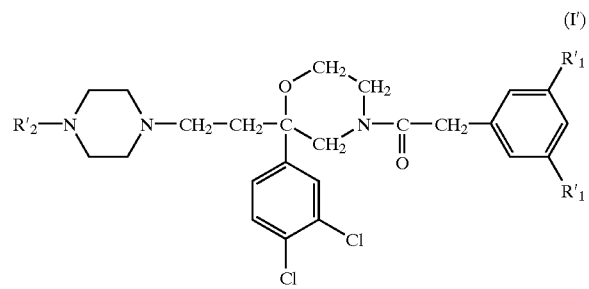

(I')

in which $R'_1$ represents a chlorine atom, a methyl, an ethyl, an isopropyl or a trifluoromethyl;

$R'_2$ represents a cyclopentyl or a cyclohexyl;

as well as the salts thereof with inorganic or organic acids, the solvates thereof and/or the hydrates thereof.

According to the present invention, the preferred compounds are those of formula:

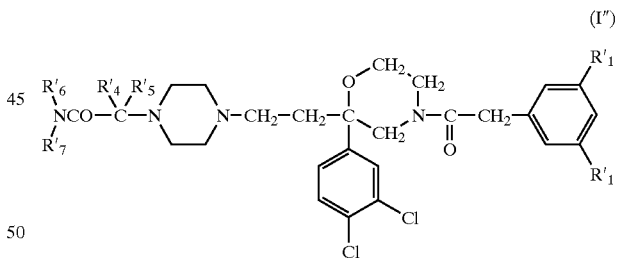

(I'')

in which:

$R'_1$ represents a chlorine atom, a methyl, an ethyl, an isopropyl or a trifluoromethyl;

$R'_4$ and $R'_5$ each represent a methyl or alternatively, together with the carbon atom to which they are attached, constitute a cyclohexyl;

$R'_6$ and $R'_7$ are similar and represent hydrogen or a methyl;

as well as the salts thereof with inorganic or organic acids, the solvates thereof and/or the hydrates thereof.

According to the present invention, the preferred compounds are those of formula:

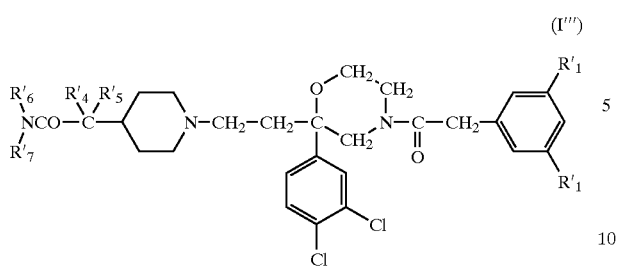

in which:

R'₁ represents a chlorine atom, a methyl, an ethyl, an isopropyl of a trifluoromethyl;

R'₄ and R'₅ each represent a methyl or alternatively, together with the carbon atom to which they are attached, constitute a cyclopropyl or a cyclohexyl;

R'₆ and R'₇ are similar and represent hydrogen or a methyl;

as well as the salts thereof with inorganic or organic acids, the solvates thereof and/or the hydrates thereof.

According to the present invention, the preferred compounds are those of formula (I), (I'), (I'') or (I''') in optically pure form.

The following compounds:

2-[2-(4-cyclohexylpiperazin-1-yl)ethyl]-2-(3,4-dichlorophenyl)-4-[2-(3,5-dimethylphenyl)-acetyl]morpholine, (−) isomer;

2-[2-(4-cyclohexylpiperazin-1-yl)ethyl]-2-(3,4-dichlorophenyl)-4-[2-(3,5-dichlorophenyl)-acetyl]morpholine, (+) isomer;

2-[2-(4-cyclohexylpiperazin-1-yl)ethyl]-2-(3,4-dichlorophenyl)-4-[2-[3,5-bis(trifluoromethyl)phenyl]acetyl]morpholine, (+) isomer;

2-[2-[4-(1-carbamoyl-1-methylethyl)piperidin-1-yl]ethyl]-2-(3,4-dichlorophenyl)-4-[2-(3,5-dimethylphenyl)acetyl]morpholine, (−) isomer;

2-[2-[4-(1-carbamoyl-1-methylethyl)piperidin-1-yl]ethyl]-2-(3,4-dichlorophenyl)-4-[2-(3,5-diethylphenyl)acetyl]morpholine, (−) isomer;

2-[2-[4-(1-carbamoylcyclohexyl)piperidin-1-yl]ethyl]-2-(3,4-dichlorophenyl)-4-[2-[3,5-bis(trifluoromethyl)-phenyl]acetyl]morpholine, (+) isomer;

2-[2-[4-(1-carbamoyl-1-methylethyl)piperazin-1-yl]ethyl]-2-(3,4-dichlorophenyl)-4-[2-(3,5-dimethylphenyl)acetyl]morpholine, (−) isomer;

2-[2-[4-(1-carbamoylcyclohexyl)piperazin-1-yl]ethyl]-2-(3,4-dichlorophenyl)-4-[2-(3,5-dimethylphenyl)-acetyl]morpholine, (−) isomer;

2-[2-[4-(1-carbamoyl-1-methylethyl)piperazin-1-yl]ethyl]-2-(3,4-dichlorophenyl)-4-[2-(3,5-diethylphenyl)acetyl]morpholine, (−) isomer;

2-[2-[4-(1-N,N-dimethylcarbamoyl-1-methylethyl)piperazin-1-yl]ethyl]-2-(3,4-dichlorophenyl)-4-[2-(3,5-diethylphenyl)acetyl]morpholine, (−) isomer;

2-[2-(4-cyclohexylpiperazin-1-yl)ethyl]-2-(3,4-dichlorophenyl)-4-[2-(3,5-diethylphenyl)-acetyl]morpholine, (−) isomer;

2-[2-[4-(1-carbamoylcyclopropyl)piperidin-1-yl]ethyl]-2-(3,4-dichlorophenyl)-4-[2-(3,5-dimethylphenyl)acetyl]morpholine, (−) isomer;

2-[2-[4-(1-carbamoyl-1-methylethyl)piperazin-1-yl]ethyl]-2-(3,4-dichlorophenyl)-4-[2-(3,5-bis(trifluoromethyl)phenyl]acetyl]morpholine, (+) isomer;

2-[2-[4-(1-carbamoyl-1-methylethyl)piperidin-1-yl]ethyl]-2-(3,4-dichlorophenyl)-4-[2-(3,5-dichlorophenyl)acetyl]morpholine, (+) isomer;

2-[2-[4-(1-carbamoyl-1-methylethyl)piperidin-1-yl]ethyl]-2-(3,4-dichlorophenyl)-4-[2-(3,5-bis(trifluoromethyl)phenyl]acetyl]morpholine, (+) isomer;

2-[2-[4-(1-carbamoyl-1-methylethyl)piperazin-1-yl]ethyl]-2-(3,4-dichlorophenyl)-4-[2-(3,5-diisopropylphenyl)acetyl]morpholine, (−) isomer; as well as the salts thereof, the solvates thereof and/or the hydrates thereof, are more particularly preferred.

According to another of its aspects, the present invention relates to a process for preparing compounds of formula (I), the salts thereof, the solvates thereof and/or the hydrates thereof, characterized in that:

1a) a compound of formula:

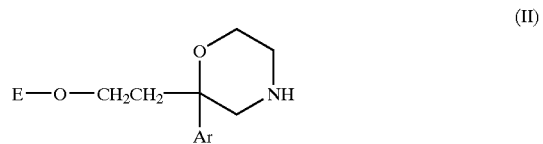

in which Ar is as defined for a compound of formula (I) and E represents hydrogen or an O-protecting group, is treated with a functional derivative of an acid of formula:

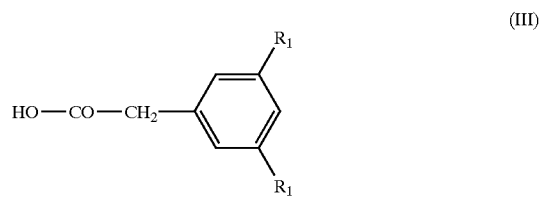

in which $R_1$ is as defined for a compound of formula (I), to give a compound of formula:

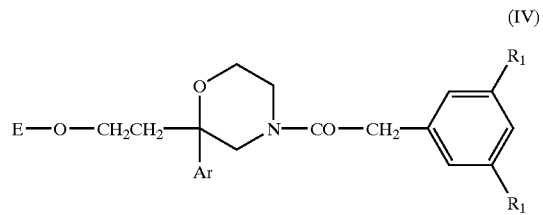

2a) optionally, when E represents a protecting group, it is removed by the action of an acid or a base, to give the alcohol of formula:

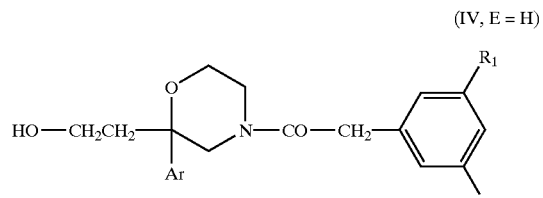

3a) the alcohol obtained in step 1a) or in step 2a) of formula (IV, E=H) is treated with a compound of formula:

  (V)

in which Y represents a methyl, phenyl, tolyl or trifluoromethyl group, to give a compound of formula:

(VI)

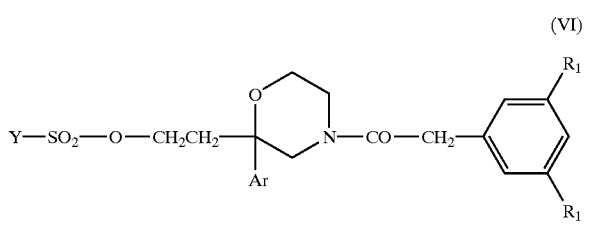

4a) the compound of formula (VI) is reacted with a compound of formula:

(VII)

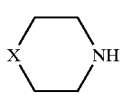

in which X is as defined for a compound of formula (I);

5a) and, optionally, the compound thus obtained is converted into one of the salts thereof with an inorganic or organic acid.

When E represents an O-protecting group, this group is chosen from conventional O-protecting groups that are well known to those skilled in the art, such as, for example, 2-tetrahydropyranyl, benzoyl or a ($C_1$–$C_4$) alkylcarbonyl.

In step 1a), the functional derivative of the acid (III) which is used is the acid itself or alternatively one of the functional derivatives which react with amines, for example an anhydride, a mixed anhydride, acid chloride or an activated ester, such as para-nitrophenyl ester.

When the acid of formula (III) itself is used, the process is performed in the presence of a coupling agent used in peptide chemistry, such as 1,3-dicyclohexylcarbodiimide or benzotriazol-1-yloxytris(dimethylamino)phosphonium hexafluorophosphate in the presence of a base such as triethylamine or N,N-diisopropylethylamine, in an inert solvent such as dichloromethane or N,N-dimethylformamide, at a temperature of between 0° C. and room temperature.

When an acid chloride is used, the reaction is carried out in an inert solvent such as dichloromethane or benzene, in the presence of a base such as triethylamine or N-methylmorpholine and at a temperature of between −60° C. and room temperature.

The compound of formula (IV) thus obtained is optionally deprotected in step 2a) according to the methods that are known to those skilled in the art. For example, when E represents a 2-tetrahydropyranyl group, the deprotection is carried out by acidic hydrolysis using hydrochloric acid in a solvent such as ether, methanol or a mixture of these solvents, or using pyridinium p-toluenesulphonate in a solvent such as methanol, or alternatively using an Amberlyst® resin in a solvent such as methanol. The reaction is carried out at a temperature between room temperature and the reflux temperature of the solvent. When E represents a benzoyl group or a ($C_1$–$C_4$)alkylcarbonyl group, the deprotection is carried out by hydrolysis in alkaline medium using, for example, an alkali metal hydroxide such as sodium hydroxide, potassium hydroxide or lithium hydroxide, in an inert solvent such as water, methanol, ethanol, dioxane or a mixture of these solvents, at a temperature of between 0° C. and the reflux temperature of the solvent.

In step 3a), the reaction of the alcohol of formula (IV, E=H) with a sulphonyl chloride of formula (V) is carried out in the presence of a base such as triethylamine, pyridine, N,N-diisopropylethylamine or N-methylmorpholine, in an inert solvent such as dichloromethane, benzene or toluene, at a temperature of between −20° C. and the reflux temperature of the solvent.

The compound of formula (VI) thus obtained is reacted in step 4a) with a compound of formula (VII). The reaction is carried out in an inert solvent such as N,N-dimethylformamide, acetonitrile, methylene chloride, toluene or isopropanol and in the presence or absence of a base. When a base is used, it is chosen from organic bases such as triethylamine, N,N-diisopropylethylamine or N-methylmorpholine or from alkali metal carbonates or bicarbonates such as potassium carbonate, sodium carbonate or sodium bicarbonate. In the absence of a base, the reaction is carried out using an excess of the compound of formula (VII) and in the presence of an alkali metal iodide such as potassium iodide or sodium iodide. The reaction is carried out at a temperature between room temperature and 100° C.

According to one variant of the process:

1b) it is performed as in step 1a) and optionally as in step 2a);

2b) the compound of formula (IV, E=H) thus obtained is oxidized in order to prepare a compound of formula:

(VIII)

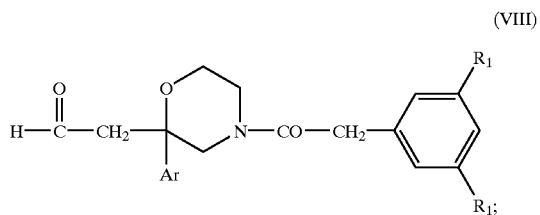

3b) the compound of formula (VIII) is reacted with a compound of formula (VII) as defined above, in the presence of an acid, followed by reduction of the intermediate iminium salt formed, by means of a reducing agent;

4b) and, optionally, the compound thus obtained is converted into one of the salts thereof with an inorganic or organic acid.

According to the variant of the process, in step 2b) an alcohol of formula (IV, E=H) is subjected to an oxidation, to give an aldehyde of formula (VIII). The oxidation reaction is carried out using, for example, oxalyl chloride, dimethyl sulphoxide and triethylamine, in a solvent such as dichloromethane and at a temperature of between −78° C. and room temperature.

Next, in step 3b), the compound of formula (VII) is reacted with an aldehyde of formula (VIII) in the presence of an acid such as acetic acid, in an inert solvent such as methanol or dichloromethane, to form in situ an intermediate imine which is reduced chemically using, for example, sodium cyanoborohydride or sodium triacetoxyborohydride, or reduced catalytically using hydrogen and a catalyst such as palladium-on-charcoal or Raney® nickel.

According to another variant of the process:

1c) the nitrogen atom of a compound of formula (II) is protected with an N-protecting group in order to obtain a compound of formula:

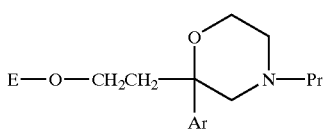
(XXXV)

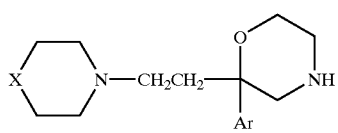
(XXXVIII)

in which Ar is as defined for a compound of formula (I), E represents hydrogen or an O-protecting group, and Pr represents an N-protecting group 2c) optionally, when E represents a protecting group, it is removed by the action of an acid or a base, in order to obtain an alcohol of formula:

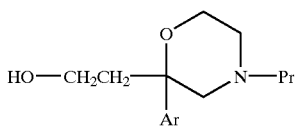
(XXXV, E = H)

3c) the alcohol obtained in step 1c) or in step 2c) of formula (XXXV, E=H) is treated with a compound of formula:

(V)

in which Y represents a methyl, phenyl, tolyl or trifluoromethyl group, in order to obtain a compound of formula:

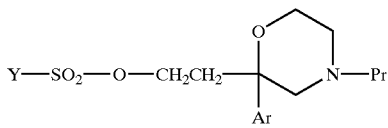
(XXXVI)

4c) the compound of formula (XXXVI) is reacted with a compound of formula:

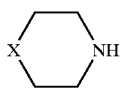
(VII)

in which X is as defined for a compound of formula (I), in order to obtain a compound of formula:

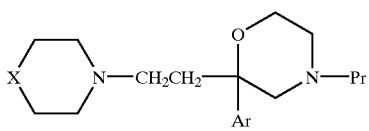
(XXXVII)

5c) the N-protecting group of the compound of formula (XXXVII) is removed in order to obtain a compound of formula:

6c) the compound of formula (XXXVIII) is treated with a functional derivative of an acid of formula:

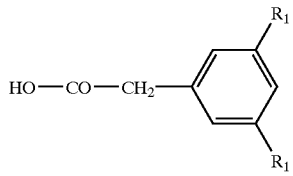
(III)

in which $R_1$ is as defined for a compound of formula (I);

7c) and, optionally, the compound thus obtained is converted into one of the salts thereof with an inorganic or organic acid.

When Pr represents an N-protecting group, this group is chosen from conventional N-protecting groups that are well known to those skilled in the art, such as, for example, the tert-butoxycarbonyl, benzyloxycarbonyl, trityl or benzyl group.

Finally, the compounds of formula (I) according to the invention are obtained.

The compounds of formula (I) thus obtained are isolated in the form of the free base or in the form of a salt, according to conventional techniques.

When the compounds of formula (I) are obtained in the form of the free base, the salification is carried out by treatment with the acid chosen in an organic solvent. Treatment of the free base, dissolved, for example, in an ether such as diethyl ether or in an alcohol such as 2-propanol or in acetone or in dichloromethane, or in ethyl acetate, with a solution of the acid chosen in one of the abovementioned solvents, gives the corresponding salt which is isolated according to conventional techniques.

Thus, for example, the hydrochloride, the hydrobromide, the sulphate, the hydrogen sulphate, the dihydrogen phosphate, the methanesulphonate, the methyl sulphate, the oxalate, the maleate, the succinate, the fumarate, the 2-naphthalenesulphonate, the benzenesulphonate, the para-toluenesulphonate, the gluconate, the citrate or the isethionate is prepared.

At the end of the reaction, the compounds of formula (I) can be isolated in the form of one of the salts thereof, for example the hydrochloride or the oxalate; in this case, if necessary, the free base can be prepared by neutralizing the said salt with an inorganic or organic base, such as sodium hydroxide or triethylamine or with an alkali metal carbonate or bicarbonate, such as sodium or potassium carbonate or bicarbonate.

The compounds of formula (II) in which E represents hydrogen or an O-protecting group are prepared according to SCHEMES 1 and 2 below in which $Pr_1$ and $Pr_2$ represent an O-protecting group as defined above for E, more particularly $Pr_1$ represents an O-protecting group which is hydrolysable in an acidic medium, $Pr_2$ represents a O-protecting group which is hydrolysable in a basic medium.

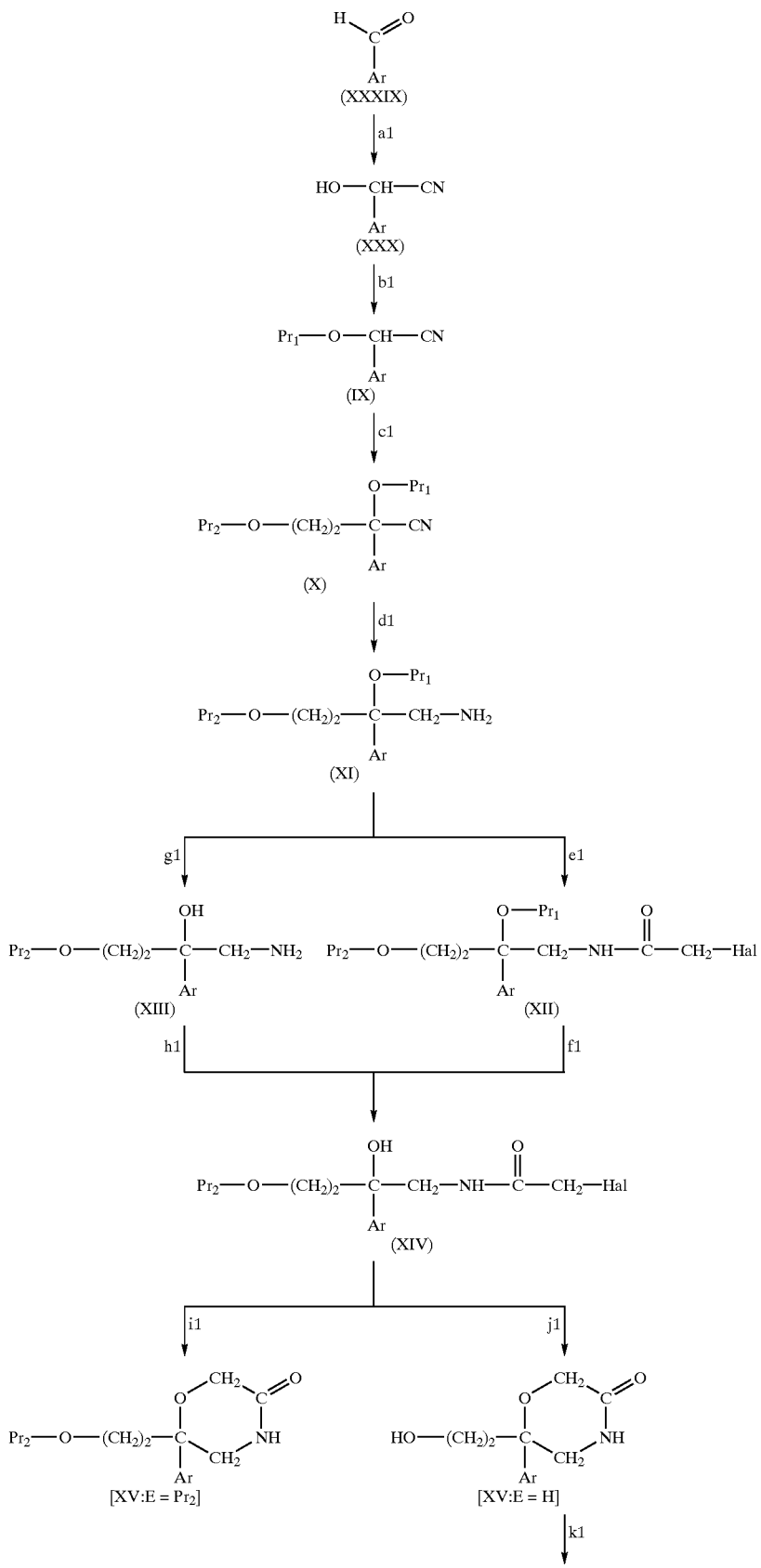

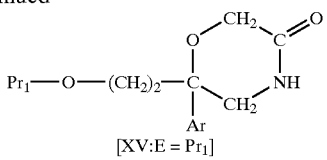

[XV:E = Pr$_1$]

SCHEME 2

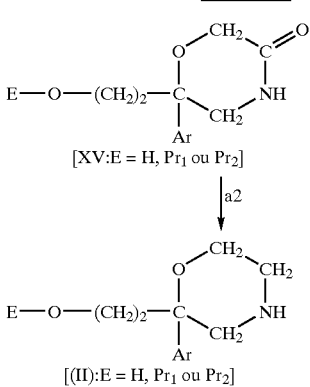

[XV:E = H, Pr$_1$ ou Pr$_2$]

↓ a2

[(II):E = H, Pr$_1$ ou Pr$_2$]

In step a1 of SCHEME 1, the synthesis of a cyanohydrin (XXXX) from an aldehyde (XXXIX) is carried out according to methods well known to those skilled in the art, such as for example that described in organic Syntheses; Wiley, N.Y., 1932; Collect. vol. 1, p. 336, or by adaptation of this method using the action of sodium metabisulphite and potassium cyanide in aqueous solution.

In step b1, the hydroxyl group of the compound (XXXX) is protected according to methods known to those skilled in the art.

The compound of formula (IX) thus obtained is treated in step c1 with a strong base such as lithium diisopropylamide, potassium tert-butoxide or sodium hydride to give a carbanion which is reacted with a compound of formula Hal-(CH$_2$)$_2$—O—Pr$_2$, in which Hal represents a halogen, preferably bromine or chlorine, in order to obtain the compound of formula (X). The reaction is carried out in an inert solvent such as an ether (for example tetrahydrofuran, diethyl ether or 1,2-dimethoxyethane) or an amide (for example N,N-dimethylformamide) or an aromatic hydrocarbon (for example toluene or xylene) at a temperature of between −70° C. and +60° C.

The nitrile derivative of formula (X) is reduced in step d1 in order to obtain the primary amine of formula (XI). This reduction can be carried out by means of hydrogen, in the presence of a catalyst such as Raney® nickel, in ethanol mixed with aqueous ammonia, or by means of a reducing agent such as lithium aluminium hydride, diisobutylaluminium hydride, borane in THF, in a solvent such as toluene, hexane, petroleum ether, xylene or tetrahydrofuran. The reaction is carried out at a temperature of between 0° C. and 70° C.

In step e1, the compound of formula (XI) is reacted with a compound of formula Hal-CO—CH$_2$-Hal in which Hal represents a halogen, preferably chlorine or bromine, in the presence of a base such as a tertiary amine (for example triethylamine, N-methylmorpholine or pyridine) in order to obtain the compound of formula (XII). The reaction is carried out in an inert solvent such as a chlorinated solvent (for example dichloromethane, dichloroethane or chloroform), an ether (for example tetrahydrofuran or dioxane) or an amide (for example N,N-dimethylformamide) at a temperature of between −70° C. and room temperature.

The O-protecting group Pr$_1$ is removed from the compound of formula (XII), in step f1, by acid hydrolysis according to the methods previously described.

Alternatively, the O-protecting group Pr$_1$ is removed from the compound of formula (XI), in step q1, by acid hydrolysis, and then the compound (XIII) thus obtained is reacted, in step h1, with a compound of formula Hal-CO—CH$_2$-Hal according to the methods described above in step e1.

The compound of formula (XIV) thus obtained is cyclized in the presence of a base in order to obtain the compound of formula (XV). When it is desired to obtain a compound of formula (XV) in which E represents a protecting group Pr$_2$, a base such as an alkali metal carbonate (for example potassium carbonate) or an alkali metal hydride (for example sodium hydride) or potassium tert-butoxide, is used in an inert solvent such as an aromatic hydrocarbon (for example xylene or toluene) or an amide (for example N,N-dimethylformamide) or an ether (for example tetrahydrofuran), at a temperature of between −30° C. and the reflux temperature of the solvent (step i1). When it is desired to obtain a compound of formula (XV) in which E represents hydrogen, a base such as an alkali metal hydroxide (for example sodium hydroxide or potassium hydroxide) is used in a concentrated aqueous solution in a solvent such as an alkanol (for example 2-propanol) or an amide (for example N,N-dimethylformamide) or a mixture of these solvents at a temperature of between room temperature and the reflux temperature of the solvent (step j1).

Optionally, a compound of formula (XV) in which E represents an O-protecting group Pr$_1$ is prepared in step k1 according to methods known to those skilled in the art.

In step a2 of SCHEME 2, a compound of formula (XV) in which E represents hydrogen or an O-protecting group, obtained according to SCHEME 1, is reduced. The reduction is carried out by means of a reducing agent such as lithium aluminium hydride, diisobutylaluminium hydride, sodium borohydride, borane in THF, in an inert solvent such as tetrahydrofuran, diethyl ether, 1,2-dimethoxyethane or toluene at a temperature of between room temperature and the reflux temperature of the solvent. The expected compound of formula (II) is thus obtained. In particular, when in the compound of formula (XV) E represents a benzoyl group, a mixture of a compound of formula (II) in which E=H and of a compound of formula (II) in which E=benzoyl is obtained during the reduction. These compounds are separated according to conventional techniques, for example by chromatography.

The compounds of formula (III) are commercially available or are prepared according to known methods.

Thus, for example, the compounds of formula (III) are prepared according to SCHEME 3 below.

SCHEME 3

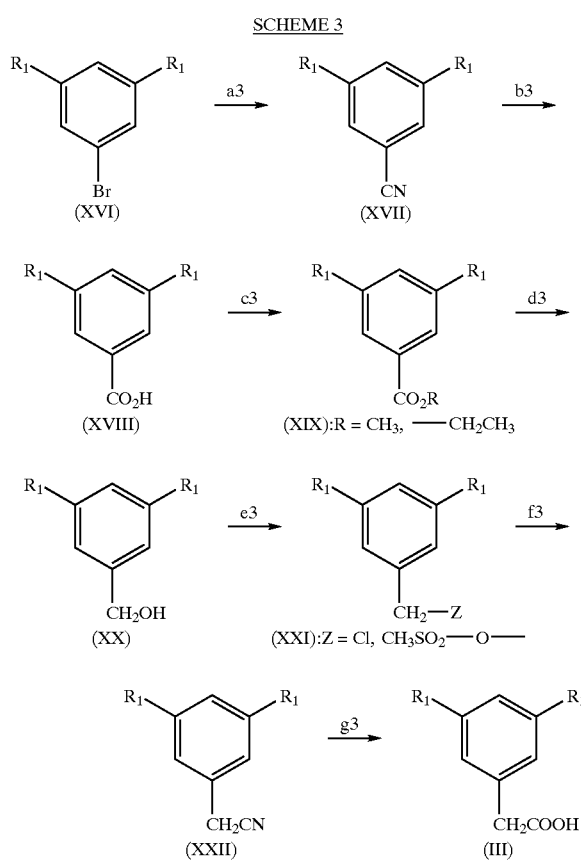

Steps a3 and b3 of SCHEME 3 are carried out according to the methods described in J. Am. Chem. Soc., 1941, 63, 3280–3282.

In step c3, an ester of formula (XIX) is prepared from an acid of formula (XVIII) according to methods known to those skilled in the art.

The ester (XIX) thus obtained is reduced in step d3 to the alcohol of formula (XX) according to methods known to those skilled in the art.

Steps e3 and f3 are carried out according to the methods described in J. Med. Chem., 1973, 16, 684–687.

The phenylacetonitrile derivatives of formula (XXII) thus obtained are hydrolysed into compounds of formula (III) according to the methods described in J. Org. Chem., 1968, 33, 4288 or in EP-A-0 714 891.

The bromo derivatives of formula (XVI) are known or are prepared according to known methods such as those described in J. Org. Chem., 1971, 36(1), 193–196, or in J. Am. Chem. Soc., 1941, 63, 3280–3282.

The compounds of formula (VII) in which X represents a group

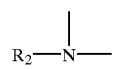

in which $R_2$ represents a $(C_1-C_6)$alkyl or a $(C_1-C_6)$ cycloalkyl are commerically available or are prepared according to known methods such as those described in J. Org. Chem. 1957, 22, 713 or J. Med. Chem., 1992, 35, 2688–2696.

The compounds of formula (VII) in which X represents a group

in which $R_2$ represents a group —$CR_4R_5CONR_6R_7$ are prepared according to SCHEME 4 below:

SCHEME 4

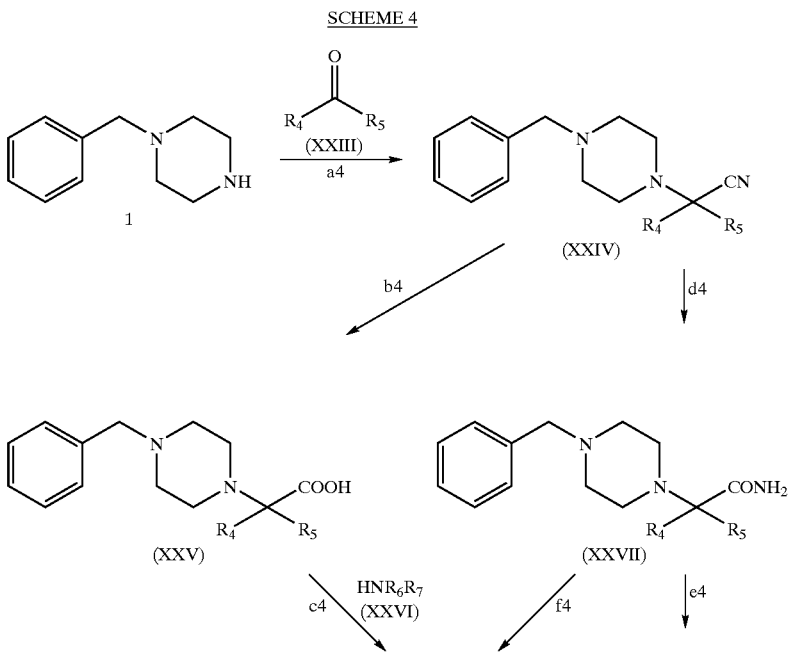

-continued

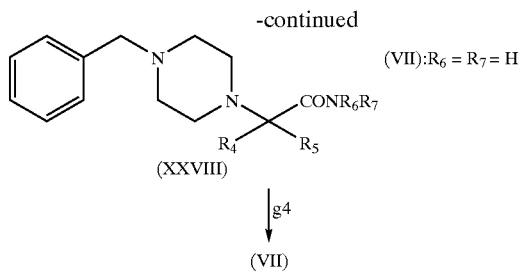

(VII): $R_6 = R_7 = H$

In step a4 of SCHEME 4, compound 1 is reacted with a ketone of formula (XXIII), in the presence of 2-hydroxyisobutyronitrile, according to the method described in Eur. J. Med. Chem., 1990, 25, 609–615.

The nitrile derivative of formula (XXIV) thus obtained is hydrolysed in step b4 according to methods known to those skilled in the art, to give an acid derivative of formula (XXV).

The acid (XXV) is reacted in step c4 with an amine of formula (XXVI) according to the conventional methods of peptide coupling, to give the derivative (XXVIII).

Alternatively, in step d4, the nitrile derivative of formula (XXIV) is hydrolysed according to the known methods, to give the carboxamide derivative of formula (XXVII), which is optionally deprotected in step e4, according to the conventional methods, to give compound (VII) in which $R_6=R_7=H$.

In step f4, by reacting the compound of formula (XXVII), in the presence of a strong base, respectively, with a $(C_1-C_3)$ alkyl halide, or successively with two $(C_1-C_3)$ alkyl halides, or with a dihalide of formula $Hal-R_6—R_7-Hal$, according to the conventional alkylation methods, a compound of formula (XXVIII) is prepared in which, respectively, $R_6$ represents a $(C_1-C_3)$alkyl and $R_7=H$, or $R_6$ and $R_7$ each independently represent a $(C_1-C_3)$alkyl, or $R_6$ and $R_7$, together with the nitrogen atom to which they are attached, constitute a heterocycle.

The compound (XXVIII) thus obtained is deprotected in step q4, according to the known methods, to give the expected compound (VII).

The compounds of formula (VII) in which X represents a group —CH—$CR_4R_5CONR_6R_7$ are prepared according to SCHEME 5 below.

SCHEME 5

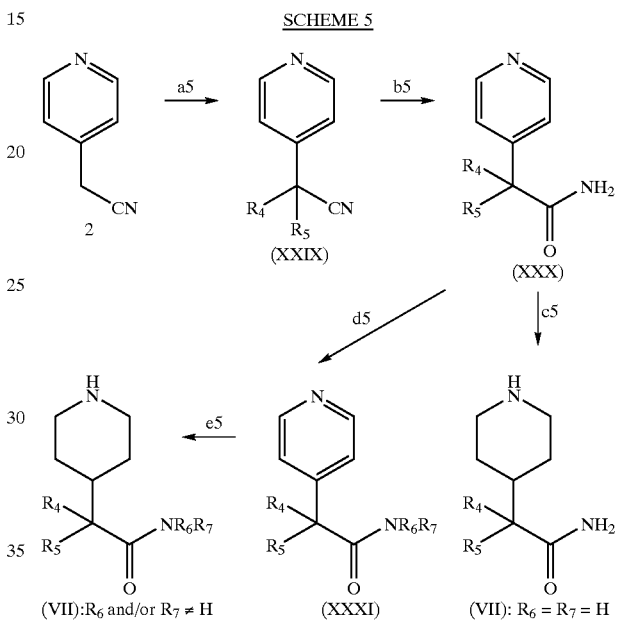

In step a5 of SCHEME 5, the reaction of compound 2, in the presence of a strong base such as sodium hydride or sodium amide, with, respectively, a linear $(C_1-C_4)$alkyl halide, or with a dihalide of formula $Hal(CH_2)_m$-Hal in which m=2 to 5 and Hal represents a halogen atom, in an inert solvent such as N,N-dimethylformamide or dichloromethane and at a temperature of between 0° C. and room temperature, according to the conventional alkylation methods, gives the compound of formula (XXIX) in which, respectively, $R_4$ and $R_5$ each represent a linear $(C_1-C_4)$alkyl or, together with the carbon atom to which they are attached, constitute a $(C_3-C_6)$cycloalkyl.

The nitrile derivative (XXIX) thus obtained is hydrolysed in step b5, according to the methods known to those skilled in the art, to give the carboxamide derivative (XXX). Optionally, in step c5, the pyridine ring is hydrogenated, in the presence of a catalyst such as platinum oxide, according to the conventional methods, to give a compound of formula (VII) in which $R_6$ and $R_7$=H.

In step d5, alkylation reaction, according to the conventional methods described previously, of the compound of formula (XXX), followed by reduction, by means of conventional catalytic hydrogenation, of the compound (XXXI) thus obtained gives a compound of formula (VII) in which $R_6$ and/or $R_7 \neq H$.

The compounds of formula (VII) in which X represent a group

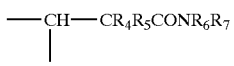

can also be obtained according to SCHEME 6 below.

SCHEME 6

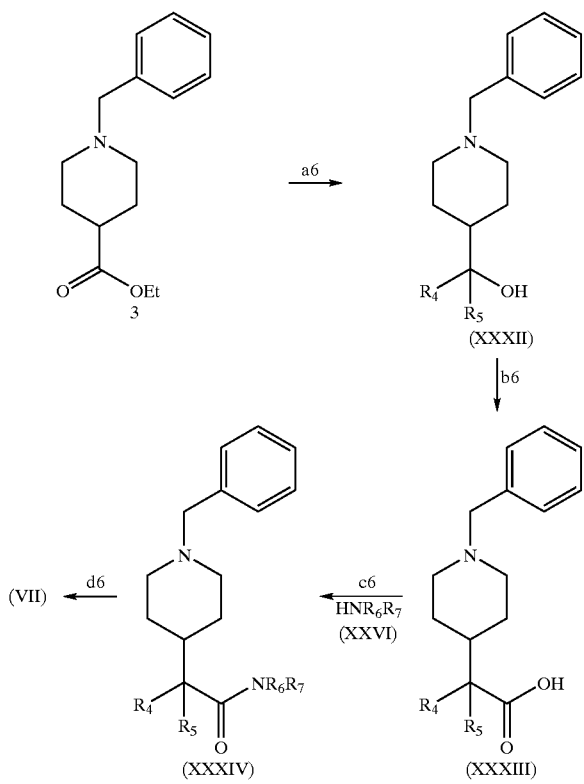

In step a6 of SCHEME 6, reaction of compound 3 with a suitable organolithium or organomagnesium derivative such as, for example, methyllithium, ethylmagnesium chloride, propylmagnesium chloride or pentane-1,5-di(magnesium chloride), according to the methods described in EP-A-0 625 509, gives the alcohol of formula (XXXII).

The alcohol (XXXII) thus obtained is oxidized in step b6 into an acid of formula (XXXIII) according to the method described in Helvetica Chimica Acta, 1972, 55 (7), 2439.

The acid (XXXIII) is reacted in step c6 with an amine of formula (XXVI) according to the conventional methods of peptide coupling, to give compound (XXXIV).

Compound (XXXIV) is deprotected in step d6, according to the known methods, to give the expected compound (VII).

Compound 3 is prepared by reacting ethyl isonipecotate with benzyl bromide, in the presence of a base, according to the conventional alkylation methods.

During any one of the steps for preparing compounds of formula (I) or the intermediate compounds of formula (II), (III) or (VII), it may be necessary and/or desirable to protect the reactive or sensitive functional groups, such as the amine, hydroxyl or carboxyl groups present on any of the molecules involved. This protection may be carried out using conventional protecting groups, such as those described in Protective Groups in Organic Chemistry, J. F. W. McOmie, ed. Plenum Press, 1973, in Protective Groups in Organic Synthesis, T. W. Greene et P. G. M. Wutts, Ed. John Wiley and sons, 1991 or in Protecting Groups, Kocienski P. J., 1994, Georg Thieme Verlag. The removal of the protecting groups may be carried out at a subsequent appropriate stage using the methods known to the those skilled in the art and which do not affect the rest of the relevant molecule.

The compounds of formula (IV) in enantiomerically pure form or in racemic form are novel and form part of the invention.

The compounds of formula (IV) in which E represents hydrogen are preferred.

The compounds of formula (IV) are prepared in step 1a) of the process according to the invention.

The compounds of formula (VI) in enantiomerically pure form or in racemic form are novel and form part of the invention.

The compounds of formula (VI) are prepared in step 3a) of the process according to the invention.

The compounds of formula (VIII) in enantiomerically pure form or in racemic form are novel and form part of the invention.

The compounds of formula (VIII) are prepared in step 2b) of the variant of the process according to the invention.

The resolution of the racemic mixtures of the compounds of formula (I) makes it possible to isolate the enantiomers.

It is however preferable to carry out the resolution of the racemic mixtures from the compound of formula (II: E=H) which is useful for the preparation of a compound of formula (I) or alternatively from an intermediate compound which is useful for the preparation of a compound of formula (II). In particular, the resolution is carried out of the racemic mixture of the compound of:

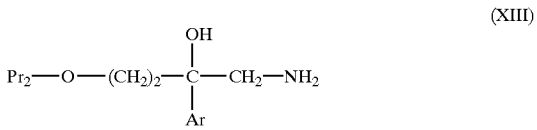

(XIII)

When the resolution of the racemates is carried out on the intermediate compounds of formula (XIII) or (II) (E=H), it may be carried out according to known methods by formation of a salt with optically active acids, for example with (+)- or (−)-tartaric acid or (+)- or (−)-10-camphorsulphonic acid. The diastereoisomers are then separated by conventional methods such as crystallization or chromatography and then, after releasing the base, the optically pure enantiomers are obtained.

The compounds of formula (I) above also comprise those in which one or more hydrogen or carbon atoms have been replaced with their radioactive isotope, for example tritium or carbon-14. Such labelled compounds are useful in research studies, of metabolism or of pharmacokinetics, in biochemical tests as receptor ligands.

The compounds according to the invention underwent biochemical tests.

The affinity of the compounds for the tachykinin receptors was evaluated in vitro by means of several biochemical tests using radio ligands:

1) The binding of [$^{125}$I] BH-SP (substance P labelled with iodine-125 using the Bolton-Hunter reagent) to the $NK_1$ receptors of human lymphoblast cells (D. G. Payan et al., J. Immunol., 1984, 133, 3260–3265).

2) The binding of [$^{125}$I] His-$NK_A$ to human $NK_2$ cloned receptors expressed by CHO cells (Y. Takeda et al., J. Neurochem., 1992, 59, 740–745).

3) The binding of [$^{125}$I] His [MePhe$^7$] $NK_B$ to the $NK_3$ receptors of rat cerebral cortex, of guinea pig cerebral cortex and of gerbil cerebral cortex as well as to the human $NK_3$ cloned receptors expressed by CHO cells (Buell et al., FEBS Letters, 1992, 299, 90–95).

The tests were carried out according to X. Emonds-Alt et al., (Eur. J. Pharmacol., 1993, 250, 403–413; Life Sci., 1995, 56, PL 27–32).

The compounds according to the invention strongly inhibit the binding of substance P to the $NK_1$ receptors of human IM9 lymphoblast cells. The inhibition constant Ki for the human lymphoblast cell receptors is of the order of $10^{-11}$M.

The inhibition constants Ki for the human $NK_2$ cloned receptors are of the order of $10^{-8}$M and the inhibition constants Ki for the human $NK_3$ cloned receptors are greater than $10^{-7}$M.

The compounds of formula (I) are powerful and selective antagonists of substance P for the human $NK_1$ receptors.

Thus, the compounds of formula (I) were also evaluated in vivo on animal models.

In guinea pig striatum, the local application of an agonist which is specific for the $NK_1$ receptors, for example [$Sar^9$, $Met(O_2)^{11}$]substance P, increases the release of acetylcholine. This release is inhibited by oral or intraperitoneal administration of the compounds according to the present invention. This test was adapted from the method described by R. Steinberg et al., J. Neurochemistry, 1995, 65, 2543–2548.

These results show that the compounds of formula (I) are active orally, that they cross the blood-brain barrier and that they are capable of blocking the action specific to the $NK_1$ receptors in the central nervous system.

The compounds of formula (I) were evaluated in the test of bronchoconstriction in guinea pigs, according to the method described by X. Emonds-Alt et al., European Journal of Pharmacology, 1993, 250, 403–413. The compounds of formula (I) administered intravenously strongly antagonize the bronchoconstriction induced by intravenous administration of septide to guinea pigs under these experimental conditions.

The in vivo pharmacological activity of the compounds of formula (I) was also evaluated in the model of hypotension in dogs, according to the method described by X. Emonds-Alt et al., Eur. J. Pharmacol., 1993, 250, 403–413. The compounds of formula (I) administered intravenously strongly inhibit the hypotension induced by intravenous administration of [$Sar^9$, $Met(O_2)^{11}$]substance P in anaesthetized dogs under these experimental conditions.

These results show that the compounds of formula (I) block the action specific to the $NK_1$ receptors in the peripheral nervous system.

The compounds of the present invention are, in particular, active principles of pharmaceutical compositions, whose toxicity is compatible with their use as medicinal products.

The compounds of formula (I) above can be used at daily doses of from 0.01 to 100 mg per kilo of body weight of the mammal to be treated, preferably at daily doses of from 0.1 to 50 mg/kg. In human beings, the dose can preferably range from 0.1 to 4000 mg per day, more particularly from 0.5 to 1000 mg depending on the age of the individual to be treated or the type of treatment: prophylactic or curative.

For their use as medicinal products, the compounds of formula (I) are generally administered in dosage units. The said dosage units are preferably formulated in pharmaceutical compositions in which the active principle is mixed with one or more pharmaceutical excipients.

Thus, according to another of its aspects, the present invention relates to pharmaceutical compositions containing, as active principle, a compound of formula (I) or one of the pharmaceutically acceptable salts, solvates and/or hydrates thereof.

In the pharmaceutical compositions of the present invention for oral, sublingual, inhaled, subcutaneous, intramuscular, intravenous, transdermal, local or rectal administration, the active principles can be administered in unit forms of administration, mixed with conventional pharmaceutical supports, to animals and to human beings. The appropriate unit forms of administration comprise oral-route forms such as tablets, gel capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

When a solid composition is prepared in the form of tablets or gel capsules, a mixture of pharmaceutical excipients which can be composed of diluents such as, for example, lactose, microcrystalline cellulose, starch, dicalcium phosphate, binders such as, for example, polyvinylpyrrolidone, hydroxypropylmethylcellulose, crumbling agents such as crosslinked polyvinylpyrrolidone, crosslinked carboxymethylcellulose, flow agents such as silica or talc, and lubricants such as magnesium stearate, stearic acid, glyceryl tribehenate or sodium stearyl fumarate, is added to the micronized or non-micronized active principle.

Wetting agents or surfactants such as sodium lauryl sulphate, polysorbate 80 or poloxamer 188 can be added to the formulation.

The tablets can be prepared by various techniques: direct tabletting, dry granulation, wet granulation, hot-melt.

The tablets may be naked or sugar-coated (for example with sucrose) or coated with various polymers or other suitable materials.

The tablets can have a flash, delayed or sustained release by preparing polymer matrices or by using specific filming polymers.

The gel capsules can be soft or hard, and coated with film or otherwise, so as to have flash, sustained or delayed activity (for example via an enteric form).

They can contain not only a solid formulation formulated as above for the tablets, but also liquid or semi-solid formulations.

A preparation in the form of a syrup or elixir can contain the active principle together with a sweetener, preferably a calorie-free sweetener, methylparaben and propylparaben as antiseptic agent, as well as a flavouring agent and a suitable colorant.

The water-dispersible powders or granules can contain the active principle as a mixture with dispersants, wetting agents or suspending agents, such as polyvinylpyrrolidone, as well as with sweeteners or flavour enhancers.

For rectal administration, use is made of suppositories which are prepared with binders that melt at the rectal temperature, for example cocoa butter or polyethylene glycols.

Aqueous suspensions, isotonic saline solutions or sterile, injectable solutions which contain pharmacologically compatible dispersants and/or solubilizing agents, for example propylene glycol, are used for parenteral, intranasal or intraocular administration.

Thus, in order to prepare an aqueous solution which can be injected intravenously, a co-solvent such as, for example, an alcohol such as ethanol or a glycol such as polyethylene glycol or propylene glycol, and a hydrophilic surfactant such as polysorbate 80 or poloxamer 188 can be used. To prepare an injectable oily solution for intramuscular administration, the active principle can be dissolved with a triglyceride or a glycerol ester.

Creams, ointments, gels, eye drops and sprays can be used for local administration. Patches in multilaminar or reservoir form in which the active principle can be in alcoholic solution, and sprays can be used for transdermal administration.

An aerosol containing, for example, sorbitan trioleate or oleic acid as well as trichlorofluoromethane, dichlorofluoromethane, dichlorotetrafluoroethane, freon substitutes or any other biologically compatible propellent gas is used for administration by inhalation; a system containing the active principle alone or combined with an excipient, in powder form, can also be used.

The active principle can also be in the form of a complex with a cyclodextrin, for example $\alpha$-, $\beta$- or $\gamma$-cyclodextrin or 2-hydroxypropyl-$\beta$-cyclodextrin.

The active principle can also be formulated in the form of microcapsules or microspheres, optionally with one or more supports or additives.

Among the sustained-release forms which are useful in the case of chronic treatments, it is possible to use implants. These can be prepared in the form of an oily suspension or in the form of a suspension of microspheres in an isotonic medium.

In each dosage unit, the active principle of formula (I) is present in the amounts suited to the daily doses envisaged. In general, each dosage unit is appropriately adjusted according to the dosage and the type of administration envisaged, for example tablets, gel capsules and the like, sachets, ampoules, syrups and the like, or drops, such that a dosage unit contains from 0.1 to 1000 mg of active principle, preferably from 0.5 to 250 mg, which needs to be administered 1 to 4 times a day.

Although these doses are examples of average situations, there may be special cases in which higher or lower doses are appropriate, and such doses also form part of the invention. According to the usual practice, the dosage which is appropriate to each patient is determined by the doctor according to the mode of administration, and the age, weight and response of the said patient.

According to another of its aspects, the present invention relates to the use of the compounds of formula (I), or of one of the pharmaceutically acceptable salts, solvates and/or hydrates thereof, for the preparation of medicinal products intended for treating any pathology in which substance P and/or the human $NK_1$ receptors are involved.

According to another of its aspects, the present invention relates to the use of the compounds of formula (I), or one of the pharmaceutically acceptable salts, solvates and/or hydrates thereof, for the preparation of medicinal products intended for treating pathologies of the respiratory, gastrointestinal, urinary, immune or cardiovascular system and of the central nervous system, as well as for pain, migraine, inflammations, nausea and vomiting, and skin diseases.

For example and in a non-limiting manner, the compounds of formula (I) are useful:

- as analgesics, in particular in the treatment of traumatic pain such as post-operative pain; neuralgia of the brachial plexus; chronic pain such as arthritic pain caused by osteoarthritis, rheumatoid arthritis or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, neuropathies induced by a chemotherapy, AIDS-related neuropathies, occipital neuralgia, geniculate neuralgia or glossopharyngeal neuralgia; the illusory pain of amputees; various forms of headache such as chronic or acute migraine, temporomandibular pain, maxillary sinus pain, facial neuralgism or odontalgia; pain experienced by cancer sufferers; pain of visceral origin; gastrointestinal pain; pain caused by compression of a nerve, pain caused by intensive sporting activity; dysmenorrhoea; menstrual pain; pain caused by meningitis or arachnoiditis; musculoskeletal pain; pain in the lower back caused by a spinal stenosis, a prolapsed disc or sciatica; pain experienced by angina sufferers; pain caused by an ankylosing spondylitis; pain associated with gout; pain associated with burns, cicatrization or pruriginous dermatosis; thalamic pain;
- as anti-inflammatory agents, in particular for treating inflammations in asthma, influenza, chronic bronchitis (in particular obstructive chronic bronchitis and COPD (chronic obstructive pulmonary disease)), coughing, allergies, bronchospasm and rheumatoid arthritis; inflammatory diseases of the gastrointestinal system, for example Crohn's disease, ulcerative colitis, pancreatitis, gastritis, intestinal inflammation, disorders caused by non-steroidal anti-inflammatory agents, inflammatory and secretory effects caused by bacterial infections, for example caused by Clostridium difficile; inflammatory skin diseases, for example herpes and eczema; inflammatory bladder diseases such as cystitis and incontinence; ophthalmic inflammations such as conjunctivitis and vitreoretinopathy; dental inflammations such as gingivitis and periodontitis;
- in the treatment of allergic diseases, in particular of the skin, such as urticaria, contact dermatitis, atopic dermatitis and respiratory diseases such as rhinitis;
- in the treatment of diseases of the central nervous system, in particular psychoses such as schizophrenia, mania and dementia; cognitive disorders such as Alzheimer's disease, anxiety, AIDS-related dementia, diabetic neuropathies; depression; Parkinson's disease; drug dependency; substance abuse; consciousness disorders, sleeping disorders, disorders of the circadian rhythm, mood disorders and epilepsy; Down's syndrome; Huntington's chorea; stress-related somatic disorders; neurodegenerative diseases such as Pick's disease or Creutzfeldt-Jacob disease; disorders associated with panic, phobia or stress;
- in the treatment of modifications of the permeability of the blood-brain barrier during inflammatory and autoimmune processes of the central nervous system, for example during AIDS-related infections;
- as a muscle relaxant and antispasmodic agent;
- in the treatment of acute or delayed and anticipated nausea and vomiting, for example nausea and vomiting induced by drugs such as the agents used in chemotherapy in the case of cancer; by radiation therapy during irradiation of the thorax or the abdomen in the treatment of cancer or carcinoidosis; by ingestion of poison; by toxins caused by metabolic or infectious disorders such as gastritis, or produced during a bacterial or viral gastrointestinal infection; during pregnancy; during vestibular disorders such as travel sickness, vertigo or Ménière's disease; in post-operative diseases; the nausea and vomiting induced by dialysis or by prostaglandins; by gastrointestinal obstructions; in reduced gastrointestinal motility; in visceral pain caused by myocardial infarction or peritonitis; in migraine; in altitude sickness; by ingestion of opiate analgesics such as morphine; in gastro-oesophageal reflux; in acidic indigestion or overconsumption of food or drink, in gastric acidity or heartburn, regurgitation, and heartburn, for example episodic or nocturnal heartburn or heartburn induced by a meal and dyspepsia;

in the treatment of diseases of the gastrointestinal system such as irritable bowel syndrome, gastric and duodenal ulcers, oesophageal ulcers, diarrhoea, hypersecretions, lymphomas, gastritis, gastro-oesophageal reflux, faecal incontinence and Hirschsprung's disease;

in the treatment of skin diseases such as psoriasis, pruritus and burns, in particular sunburn;

in the treatment of diseases of the cardiovascular system such as hypertension, the vascular aspects of migraine, oedema, thrombosis, angina pectoris, vascular spasms, circulatory diseases caused by vasodilation, Raynaud's disease, fibrosis, collagen diseases and atherosclerosis;

in the treatment of small-cell lung cancer; breast cancer; cerebral tumours; adenocarcinomas of the urogenital sphere; in adjuvant treatment to prevent metastases;

demyelination diseases such as multiple sclerosis or amyotrophic lateral sclerosis;

in the treatment of diseases of the immune system associated with suppression or stimulation of the functions of the immune cells, for example rheumatoid arthritis, psoriasis, Crohn's disease, diabetes, lupus and rejection reactions after transplantation;

in the treatment of miction disorders, in particular pollakiuria;

in the treatment of histiocytic reticulosis, for instance in lymphatic tissues;

as an anorexigenic agent;

in the treatment of emphysema; Reiter's disease; haemorrhoids;

in the treatment of ocular disorders such as glaucoma, ocular hypertension, myosis and excessive lachrymal secretion;

in the treatment or prevention of an epileptic fit, cranial trauma, spinal cord trauma, cerebral ischaemic lesions caused by vascular attack or occlusion;

in the treatment of disorders of heart rate and cardiac rhythm, in particular those occasioned by pain or stress;

in the treatment of sensitive skin and for preventing or combating irritation of the skin or mucous membranes, dandruff, erythema or pruritus;

in the treatment of neurological skin disorders such as lichens, prurigo, pruriginous toxidermia and severe pruritus of neurogenic origin;

in the treatment of ulcers and of all diseases caused by Helicobacter pylori or a urease-positive gram-negative bacterium;

in the treatment of diseases caused by angiogenesis or in which angiogenesis is a symptom;

in the treatment of ocular and/or palbebral algia and/or ocular or palbebral dysesthesia;

as an antiperspirant.

The present invention also includes a method for treating the said complaints at the doses indicated above.

The pharmaceutical compositions according to the present invention can also contain other active products that are useful for treating the diseases or disorders indicated above, for example bronchodilators, antitussive agents, antihistamines, anti-inflammatory agents, anti-emetic agents and chemotherapy agents.

The following Preparations and Examples illustrate the invention without however limiting it.

The following abbreviations are used in the Preparations and in the Examples:

DMF: dimethylformamide

DMSO: dimethyl sulphoxide

DCM: dichloromethane

THF: tetrahydrofuran hydrochloric ether: saturated solution of hydrochloric acid in ether BOP: benzotriazol-1-yloxytris(dimethylamino)-phosphonium hexafluorophosphate m.p.: melting point RT: room temperature b.p.: boiling point silica H: 60H silica gel sold by Merck (Darmstad).

The proton nuclear magnetic resonance ($^1$H NMR) spectra are recorded at 200 MHz in DMSO-$d_6$, using the DMSO-$d_6$ peak as reference. The chemical shifts δ are indicated in parts per million (ppm). The signals observed are expressed as follows:

s: singlet; se: broad singlet; t: triplet; qd: quartet;

m: unresolved complex; mt: multiplet.

PREPARATION 1.1 AND 1.2

2-[2-(Benzoyloxy)ethyl]-2-(3,4-dichlorophenyl) morpholine, (–) Isomer (Preparation 1.1) and 2-(3,4-Dichlorophenyl)-2-(2-hydroxyethyl)morpholine, (–) Isomer (Preparation 1.2)

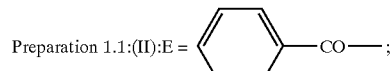

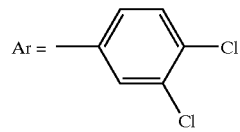

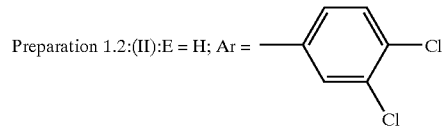

A) 2-(3,4-Dichlorophenyl)-2-hydroxyacetonitrile.

A mixture of 70 g of 3,4-dichlorobenzaldehyde, 90 g of $Na_2S_2O_5$ in 300 ml of water is left stirring overnight at RT. The reaction mixture is cooled to 0° C., a solution of 52 g of KCN in 100 ml of water is added dropwise and the mixture is left stirring while the temperature is allowed to rise to RT. The reaction mixture is extracted with ether, the organic phase washed with water, dried over $Na_2SO_4$ and the solvent evaporated off under vacuum. 76 g of the expected product are obtained, which product is used as it is.

B) 2-(3,4-Dichlorophenyl)-2-(tetrahydropyran-2-yloxy) acetonitrile.

A solution of 76 g of the compound obtained in the preceding step and 0.25 g of p-toluenesulphonic acid monohydrate in 300 ml of DCM is cooled to 0° C., a solution of 39 g of 3,4-dihydro-2H-pyran in 50 ml of DCM is added dropwise and the mixture is left stirring while the temperature is allowed to rise to RT. The reaction mixture is washed with a saturated NaHCO$_3$ solution, with water, the organic phase dried over Na$_2$SO$_4$ and the solvent evaporated under vacuum. 33 g of the expected product are obtained after crystallization at 0° C. from pentane, m.p.=61° C.

C) 4-(Benzoyloxy)-2-(3,4-dichlorophenyl)-2-(tetrahydropyran-2-yloxy)butanenitrile.

56 ml of a 2M solution of lithium diisopropylamide in THF is cooled to −60° C., a solution of 32 g of the compound obtained in the preceding step in 50 ml of THF is added dropwise and the mixture is left stirring for 1 hour at −60° C. A solution of 25.4 g of 2-bromoethyl benzoate in 50 ml of THF is then added dropwise at −60° C. and the mixture is left stirring while the temperature is allowed to rise to RT. The reaction mixture is concentrated under vacuum, the residue extracted with ether, the organic phase washed with water, with a buffer solution pH=4, dried over Na$_2$SO$_4$ and the solvent evaporated under vacuum. The residue is chromatographed on silica, eluting with the toluene/AcOEt (100/5; v/v) mixture. 34 g of the expected product are obtained, which product is used as it is.

D) 4-(Benzoyloxy)-2-(3,4-dichlorophenyl)-2-(tetrahydropyran-2-yloxy)butylamine.

A mixture of 34 g of the compound obtained in the preceding step, 10 g of Raney® nickel in 400 ml of EtOH and 40 ml of a concentrated solution of aqueous ammonia is hydrogenated at RT and at atmospheric pressure. The catalyst is filtered off and the filtrate is concentrated under vacuum. The residue is taken up in water, extracted with ether, the organic phase washed with a saturated NaCl solution, dried over Na$_2$SO$_4$ and the solvent evaporated under vacuum. The residue is chromatographed on H silica, eluting with the gradient of of the DCM/MeOH mixture from (100/1; v/v) to (100/3; v/v). 16 g of the expected product are obtained, which product is used as it is.

E) 4-(Benzoyloxy)-2-(3,4-dichlorophenyl)-2-hydroxybutylamine Hydrochloride.

A saturated solution of HCl gas in ether is added at RT, to pH=1, to a solution of 12 g of the compound obtained in the preceding step in 50 ml of MeOH and the mixture is left stirring for 1 hour at RT. The reaction mixture is concentrated under vacuum, the residue taken up in DCM, the precipitate formed drained and washed with ether. 3.4 g of the expected product are obtained after recrystallization from 2-propanol, m.p.=200–204° C.

F) 4-(Benzoyloxy)-2-(3,4-dichlorophenyl)-2-hydroxybutylamine, (−) Isomer.

A solution of 56.2 g of (1S)-(+)-10-camphorsulphonic acid in 660 ml of 2-propanol is heated under reflux and then a solution of 78 g of the compound obtained in the preceding step, in free base form, in 660 ml of 2-propanol is added in a single portion and the mixture is left stirring overnight, allowing the temperature to return to RT. The crystals formed are drained, they are washed with 2-propanol, then with ether and they are dried under vacuum. 115 g of the camphorsulponic acid salt are obtained. The salt thus obtained is recrystallized from 3000 ml of 2-propanol and 100 g of the camphorsulphonic acid salt are obtained after stirring overnight at RT, draining, washing and drying of the crystals formed. The salt thus obtained is again recrystallized from 3000 ml of EtOH 100 and 32 g of the camphorsulphonic acid salt are obtained after draining, washing and drying of the crystals formed.

$\alpha_D^{20}$=−17.3° (c=1; MeOH).

30 g of the salt thus obtained are taken up in a 10% Na$_2$CO$_3$ solution, extracted with AcOEt, the organic phase washed with water to neutral pH, dried over Na$_2$SO$_4$ and the solvent evaporated off under vacuum. 17.72 g of the expected producct are obtained after drying under vacuum at 60° C., m.p.=101° C.

$\alpha_D^{20}$=−49.1° (c=1; MeOH).

G) N-(2-Chloroacetyl)-4-(benzoyloxy)-2-(3,4-dichlorophenyl)-2-hydroxybutylamine, (−) Isomer.

A solution of 11.76 g of the compound obtained in the preceding step and 3.33 g of triethylamine in 150 ml of DCM is cooled to 0° C., a solution of 3.75 g of chloroacetyl chloride is added dropwise and the mixture is left stirring for 5 minutes. The reaction mixture is concentrated under vacuum, the residue extracted with AcOEt, the organic phase washed with water, with a buffer solution pH=2, with a saturated NaCl solution, dried over Na$_2$SO$_4$ and the solvent evaporated off under vacuum. 14 g of the expected product are obtained after crystallization from the ether iso/pentane mixture, m.p.=72–74° C.

$\alpha_D^{20}$=−28° (c=1; MeOH).

H) 6-[2-(Benzoyloxy)ethyl]-6-(3,4-dichlorophenyl) morpholin-3-one, (−) Isomer.

A solution of 13.5 g of the compound obtained in the preceding step in 400 ml of THF is cooled to −30° C., 7.02 g of potassium tert-butoxide are added in a single portion and the mixture is left stirring for 20 minutes at −30° C. The reaction mixture is concentrated under vacuum in the cold state, the residue extracted with AcOEt, the organic phase washed with a buffer solution at pH=2, with water, with a saturated NaCl solution, dried over Na$_2$SO$_4$ and the solvent evaporated off under vacuum. 11.87 g of the expected product are obtained after crystallization from the ether iso/pentane mixture, m.p.=134–137° C. $\alpha_D^{20}$=−49° (c=1; MeOH).

I) 2-[2-(Benzoyloxy)ethyl]-2-(3,4-dichlorophenyl) morpholine, (−) Isomer (Preparation 1.1) and 2-(3,4-Dichlorophenyl)-2-(2-hydroxyethyl)morpholine, (−) Isomer (Preparation 1.2).

A solution of 19.5 g of the compound obtained in the preceding step in 100 ml of THF is added, at RT and dropwise, to 250 ml of a 1M solution of borane in THF and then the mixture is heated under reflux for 3 hours. 120 ml of boiling MeOH are then added dropwise and the refluxing is continued for 30 minutes. The reaction mixture is cooled on an ice bath, 50 ml of a hydrochloric ether solution are added and the mixture is left stirring overnight at RT. The reaction mixture is concentrated under vacuum, the residue taken up in a 10% Na$_2$CO$_3$ solution, extracted with AcOEt, the organic phase washed with water, dried over Na$_2$SO$_4$ and the solvent evaporated off under vacuum. The residue is chromatographed on H silica gel, eluting with the gradient of the DCM/MeOH mixture from (100/3; v/v) to (100/5; v/v). The two compounds are separated:

the least polar: compound of preparation 1.1, m=10.4 g, in oil form. $\alpha_D^{20}$=−17° (c=0.5; MeOH).

the most polar: compound of preparation 1.2, m=5.3 g, in oil form. $\alpha_D^{20}$=−20° (c=0.5; MeOH).

PREPARATION 2.1

3,5-Dichlorophenylacetic Acid (III): R$_1$=Cl.

A) 3,5-Dichlorobenzyl Chloride.

A solution of 12.5 g of thionyl chloride in ml of chloroform is added dropwise at RT to a solution of 14.5 g of 3,5-dichlorobenzyl alcohol in 150 ml of chloroform and then the mixture is heated at 40–50° C. for 8 hours and is left stirring overnight at RT. The mixture is concentrated under vacuum and 16 g of the expected product are obtained, which product is used as it is.

B) 3,5-Dichlorophenylacetonitrile.

A solution of 6.5 g of potassium cyanide in 50 ml of water is added to a solution of 16 g of the compound obtained in the preceding step in 50 ml of EtOH and the mixture is heated under reflux for 4 hours. The mixture is concentrated under vacuum, the residue is taken up in water, extracted with ether, the organic phase is washed with water, dried over $Na_2SO_4$ and the solvent is evaporated off under vacuum. The residue is chromatographed on H silica, eluting with the heptane/toluene (50/50; v/v) mixture and then with toluene. 7 g of the expected product are obtained, which product is used as it is.

C) 3,5-Dichlorophenylacetic Acid.

A solution of 8.4 g of KOH in 10 ml of water is added to a solution of 7 g of the compound obtained in the preceding step in 50 ml of EtOH and then the mixture is heated under reflux for 5 hours. The mixture is concentrated under vacuum, the residue is taken up in water, the aqueous phase is washed with ether, the aqueous phase is acidified to pH=1 by addition of concentrated HCl and the mixture is left stirring overnight at RT. The crystallized product formed is drained, washed with water and dried under vacuum at 60° C. 7 g of the expected product are obtained, m.p.= 112–114.5° C.

PREPARATION 2.2

3,5-Diethylphenylacetic Acid (III): $R_1=CH_2CH_3$.

A) 3,5-Diethylbromobenzene.

A mixture of 20 g of 4-bromo-2,6-diethylaniline, 160 ml of acetic acid, 100 ml of a concentrated HCl solution, 30 ml of water and 100 ml of EtOH is cooled to −5° C., a solution of 6.6 g of sodium nitrite in 25 ml of water is added dropwise and the mixture is left stirring for 30 minutes at RT. The reaction mixture is poured over 170 ml of 50% $H_3PO_2$ cooled to 0° C., the mixture is left stirring for 2 hours at 0° C. and then for 48 hours at RT. The reaction mixture is extracted with ether, the organic phase washed with water, with a 1N NaOH solution, with water, dried over $Na_2SO_4$ and the solvent evaporated off under vacuum. The residue is chromatographed on silica gel, eluting with cyclohexane. 18 g of the expected product are obtained.

B) 3,5-Diethylbenzonitrile.

A mixture of 24.7 g of the compound obtained in the preceding step and 12 g of copper(I) cyanide in 70 ml of DMF is heated for 15 hours under reflux. After cooling to RT, the reaction mixture is poured over 50 ml of water and left stirring at RT until a gum is formed. The mixture is cooled on an ice bath, 150 ml of ethylenediamine are added and the mixture is left stirring for 2 hours at RT. The mixture is extracted with AcOEt, the organic phase is washed with water, dried over $Na_2SO_4$ and the solvent is evaporated off under vacuum. The residue is chromatographed on silica gel, eluting with the cyclohexane/AcOEt (95/5; v/v) mixture. 12 g of the expected product are obtained.

C) 3,5-Diethylbenzoic Acid.

A solution of 22 g of KOH in 15 ml of water is added to a solution of 12 g of the compound obtained in the preceding step in 60 ml of EtOH and the mixture is heated under reflux for 24 hours. The reaction mixture is concentrated under vacuum, the residue extracted with water, the aqueous phase washed with ether, the aqueous phase acidified to pH=2 by addition of concentrated HCl, the precipitate formed drained, washed with water and dried under vacuum. 13 g of the expected product are obtained.

D) 3,5-Diethylbenzoic Acid Methyl Ester.

A mixture of 13 g of the compound obtained in the preceding step in 90 ml of MeOH and 10 drops of $H_2SO_4$ is heated under reflux for 48 hours. The reaction mixture is concentrated under vacuum, the residue is taken up in water, neutralized by addition of a 10% $NaHCO_3$ solution, extracted with water, the organic phase washed with a 10% $NaHCO_3$ solution, with water, dried over $Na_2SO_4$ and the solvent evaporated off under vacuum. 12 g of the expected product are obtained.

E) 3,5-Diethylbenzyl Alcohol.

A suspension of 2.5 g of lithium aluminium hydride in 50 ml of THF is cooled to 0° C., a solution of 12 g of the compound obtained in the preceding step in 50 ml of THF is added dropwise and the mixture is left stirring for 30 minutes. The reaction mixture is hydrolysed by addition of 2.5 ml of water, 2.5 ml of 4N NaOH and 7.5 ml of water. The mineral salts are filtered and the filtrate is concentrated under vacuum. 10.9 g of the expected product are obtained, which product is used as it is.

F) 3,5-Diethylbenzyl Methanesulphonate

A solution of 8.4 g of methanesulphonyl chloride in 50 ml of DCM is added dropwise at RT to a solution of 10.9 g of the compound obtained in the preceding step and 7.4 g of triethylamine in 100 ml of DCM and the mixture is left stirring for 30 minutes. The reaction mixture is concentrated under vacuum, the residue is taken up in water, extracted with ether, the organic phase washed with water, dried over $Na_2SO_4$ and the solvent evaporated off under vacuum. 16 g of the expected product are obtained, which product is used as it is.

G) 3,5-Diethylphenylacetonitrile.

A solution of 5.15 g of potassium cyanide in ml of water is added to a solution of 16 g of the compound obtained in the preceding step in 100 ml of DMF and the mixture is heated at 80° C. for 1 hour. The reaction mixture is concentrated under vacuum, the residue taken up in water, extracted with ether, the organic phase washed with water, dried over $Na_2SO_4$ and the solvent evaporated off under vacuum. The residue is chromatographed on H silica gel, eluting with DCM. 3 g of the expected product are obtained.

H) 3,5-Diethylphenylacetic acid.

A solution of 7.8 g of KOH in 10 ml of water is added to a solution of 3 g of the compound obtained in the preceding step in 50 ml of EtOH and then the mixture is heated under reflux for 5 hours. The mixture is concentrated under vacuum, the residue taken up in water, the aqueous phase washed with ether, the aqueous phase acidified to pH=1 by addition of concentrated HCl and the mixture is left stirring overnight at RT. The crystallized product formed is drained, washed with water and dried under vacuum. 2.5 g of the expected product are obtained.

$^1$H NMR: δ (ppm): 1.1: t: 6H; 2.4: qd: 4H; 3.4: s: 2H; 6.8: m: 3H; 12.2s: 1H.

PREPARATION 2.3

3,5-Diisopropylphenylacetic Acid

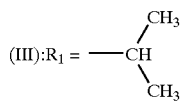

A) 4-Bromo-2,6-diisopropylamine.

A solution of 17.7 g of 2,6-diisopropylamine in 50 ml of MeOH and 10 ml of acetic acid is cooled on an ice bath, a solution of 16 g of bromine in 50 ml of acetic acid is added dropwise while the temperature is maintained below 15° C. and the mixture is left stirring for 2 hours at RT. The reaction mixture is concentrated under vacuum, the residue extracted with ether, the organic phase washed several times with water, dried over Na$_2$SO$_4$ and the solvent evaporated under vacuum. 25 g of the expected product are obtained.

B) 3,5-Diisopropylbromobenzene.

A mixture of 25 g of the compound obtained in the preceding step in 180 ml of acetic acid, 120 ml of water and 35 ml of a concentrated HCl solution is cooled to 0° C., a solution of 7.6 g of sodium nitrite in 30 ml of water is added dropwise while the temperature is maintained below 5° C. and the mixture is left stirring for 30 minutes at −5° C. The reaction mixture is poured over 75 ml of 50% H$_3$PO$_2$ cooled to 0° C. and the mixture is left stirring overnight, the temperature being allowed to return to RT. The reaction mixture is extracted with ether, the organic phase washed with water, dried over Na$_2$SO$_4$ and the solvent evaporated off under vacuum. The residue is chromatographed on silica gel, eluting with cyclohexane. 16.2 g of the expected product are obtained.

C) 3,5-Diisopropylbenzonitrile.

A mixture of 16.2 g of the compound obtained in the preceding step and 6.95 g of copper(I) cyanide in 50 ml of DMF is heated for 18 hours under reflux. After cooling to RT, the reaction mixture is poured over 150 ml of water and left stirring for 30 minutes at RT. The mixture is cooled on an ice bath, 150 ml of ethylenediamine are added and the mixture is left stirring for 2 hours at RT. The mixture is extracted with AcOEt, the organic phase washed with water, dried over Na$_2$SO$_4$ and the solvent evaporated off under vacuum. The residue is chromatographed on silica gel, eluting with the cyclohexane/AcOEt (100/5; v/v) mixture. 5.5 g of the expected product are obtained.

D) 3,5-Diisopropylbenzoic Acid.

A solution of 6.7 g of KOH in 10 ml of water is added to a solution of 5.5 g of the compound obtained in the preceding step in 50 ml of EtOH and the mixture is heated under reflux for 18 hours. The reaction mixture is concentrated under vacuum, the residue taken up in water, the aqueous phase washed with ether, the aqueous phase acidified to pH=1 by addition of concentrated HCl, the precipitate formed drained, washed with water and dried. 5.4 g of the expected product are obtained.

E) 3,5-Diisopropylbenzoic Acid Ethyl Ester.

A mixture of 5.4 g of the compound obtained in the preceding step in 100 ml of EtOH and 10 drops of H$_2$SO$_4$ is heated under reflux for 18 hours. The reaction mixture is concentrated under vacuum, the residue taken up in water, neutralized by addition of a 10% NaHCO$_3$ solution, extracted with ether, the organic phase washed with water, dried over Na$_2$SO$_4$ and the solvent evaporated off under vacuum. 6 g of the expected product are obtained.

F) 3,5-Diisopropylbenzyl Alcohol.

A solution of 6 g of the compound obtained in the preceding step in 50 ml of THF is added dropwise at RT to a suspension of 1 g of lithium aluminium hydride in 25 ml of THF and the mixture is left stirring for 30 minutes. The reaction mixture is hydrolysed by addition of 1 ml of water, 1 ml of 4N NaOH and then 3 ml of water. The mineral salts are filtered and the filtrate is concentrated under vacuum. The residue is extracted with DCM, the organic phase washed with water, dried over Na$_2$SO$_4$ and the solvent evaporated under vacuum. The residue is chromatographed on silica gel, eluting with the cyclohexane/AcOEt (100/5; v/v) mixture. 4.4 g of the expected product are obtained.

G) 3,5-Diisopropylbenzyl Methanesulphonate.

A solution of 2.88 g of methanesulphonyl chloride in 10 ml of DCM is added dropwise at RT to a solution of 4.4 g of the compound obtained in the preceding step and 2.5 g of triethylamine in 50 ml of DCM and the mixture is left stirring for 30 minutes. The reaction mixture is washed with water, the organic phase dried over Na$_2$SO$_4$ and the solvent evaporated off under vacuum. 6.2 g of the expected product are obtained.

H) 3,5-Diisopropylphenylacetonitrile.

A solution of 1.8 g of potassium cyanide in 20 10 ml of water is added to a solution of 6.2 g of the compound obtained in the preceding step in 40 ml of EtOH and the mixture is heated under reflux for 3 hours. The reaction mixture is concentrated under vacuum, the residue taken up in water, extracted with ether, the organic phase washed with water, dried over Na$_2$SO$_4$ and the solvent evaporated off under vacuum. The residue is chromatographed on silica gel, eluting with the cyclohexane/AcOEt (100/5; v/v) mixture. 2.2 g of the expected product are obtained.

I) 3,5-Diisopropylphenylacetic Acid.

A solution of 3.8 g of KOH in 10 ml of water is added to a solution of 2.2 g of the compound obtained in the preceding step in 40 ml of EtOH and the mixture is heated under reflux for 5 hours. The reaction mixture is concentrated under vacuum, the residue taken up in water, the aqueous phase washed with ether, the aqueous phase acidified to pH=1 by addition of concentrated HCl, extracted with DCM, the organic phase washed with water, dried over Na$_2$SO$_4$ and the solvent evaporated off under vacuum. 2 g of the expected product are obtained.

PREPARATION 3.1

2-(Piperidin-4-yl)isobutyramide Hydrochloride

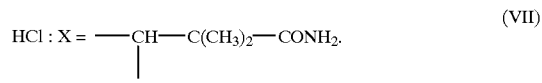

(VII)

A) 2-Methyl-2-(pyridin-4-yl)propionitrile.

A mixture of 3 g of pyridin-4-ylacetonitrile hydrochloride in 50 ml of DMF is cooled to 0° C., 2.6 g of 60% sodium hydride in oil are added in small portions and the mixture is left stirring for 2 hours at RT. The reaction mixture is cooled on an ice bath, 6 g of methyl iodide are added dropwise and the mixture is left stirring overnight at RT. The reaction mixture is poured over a water/ice mixture, extracted with ether, the organic phase washed with a saturated NaCl solution, dried over MgSO$_4$, filtered and the solvent evaporated off under vacuum. The residue is chromatographed on H silica gel, eluting with DCM and then with the DCM/MeOH (98/2; v/v) mixture. 2.39 g of the expected product are obtained in the form of an oil which crystallizes.

B) 2-(Pyridin-4-yl)isobutyramide Hydrochloride.

A mixture of 2.39 g of the compound obtained in the preceding step and 10 ml of a concentrated H$_2$SO$_4$ solution is heated at 100° C. for 15 minutes. The reaction mixture is cooled to RT, 50 g of ice are added, the mixture is alkalinized to pH=14 by addition of a concentrated NaOH solution, the mineral salts are filtered, the filtrate extracted with AcOEt and then with DCM, the combined organic phases dried over MgSO$_4$, filtered and the solvents evaporated off under vacuum (m.p.=134° C., base). The product obtained is dissolved in acetone, the mixture is acidified to pH=1 by addition of hydrochloric ether and the precipitate formed is drained. 2.9 g of the expected product are obtained.

C) 2-(Piperidin-4-yl)isobutyramide Hydrochloride.

A mixture of 2.9 g of the compound obtained in the preceding step, 1 g of PtO$_2$ and 50 ml of MeOH is hydrogenated for 3 days, at 60° C., at a pressure of 60 bar. The catalyst is filtered off on Celite®, and the filtrate is washed with MeOH and concentrated under vacuum. The residue is taken up in acetonitrile, the precipitate formed drained, washed with acetonitrile and then with ether. 2.5 g of the expected product are obtained, m.p.>260° C.

PREPARATION 3.2

2-(Piperazin-1-yl)isobutyramide Dihydrochloride

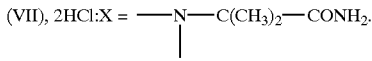

(VII), 2HCl:X = —N—C(CH$_3$)$_2$—CONH$_2$.

A) 2-(4-Benzylpiperazin-1-yl)-2-methylpropionitrile.

4.5 ml of acetone, 20 g of dry MgSO$_4$, 10 g of N,N-dimethylacetamide, 10 g of 1-benzylpiperazine and 9.5 ml of 2-hydroxyisobutyronitrile are mixed and the mixture is heated at 45° C. for 48 hours, with vigorous stirring. The reaction mixture is poured over ice and left stirring for 30 minutes. The mixture is extracted with ether, the organic phase washed several times with water, dried over Na$_2$SO$_4$ and the solvent evaporated off under vacuum. 13 g of the expected product are obtained.

B) 2-(4-Benzylpiperazin-1-yl)isobutyramide Dihydrochloride.

A mixture of 13 g of the compound obtained in the preceding step and 130 ml of a 90% H$_2$SO$_4$ solution is rapidly heated at 110° C. for 30 minutes. After cooling to RT, the reaction mixture is poured over ice, alkalinized to pH=10 by addition of a concentrated NH$_4$OH solution and the crystallized product formed is drained. The product is dissolved in DCM, the organic phase dried over MgSO$_4$ and the solvent evaporated off under vacuum. The product is taken up in hydrochloric ether and the precipitate formed is drained. 9.5 g of the expected product are obtained.

C) 2-(Piperazin-1-yl)isobutyramide Dihydrochloride.

A mixture of 1.3 g of the compound obtained in the preceding step and 0.18 g of 10% palladium-on-charcoal in 30 ml of 95% EtOH is hydrogenated overnight at RT and at atmospheric pressure. The catalyst is filtered off on Celite® and the filtrate is concentrated under vacuum. 0.6 g of the expected product is obtained.

PREPARATION 3.3

1-(Piperazin-1-yl)cyclohexanecarboxamide Dihydrochloride

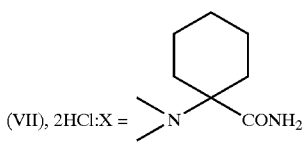

(VII), 2HCl:X = >N CONH$_2$

A) 1-(4-Benzylpiperazin-1-yl)cyclohexanecarbonitrile.

5.7 g of cyclohexanone, 20 g of dry MgSO$_4$, 10 g of N,N-dimethylacetamide, 10 g of 1-benzylpiperazine and 9.5 ml of 2-hydroxyisobutyronitrile are mixed and the mixture is heated at 45° C. for 48 hours, with vigorous stirring. The reaction mixture is poured over ice and left stirring for 30 minutes. The mixture is extracted with ether, the organic phase washed several times with water, dried over Na$_2$SO$_4$ and the solvent evapoared off under vacuum. 15 g of the expected product are obtained.

B) 1-(4-Benzylpiperazin-1-yl)cyclohexanecarboxamide Dihydrochloride.

This compound is prepared according to the procedure described in step B of Preparation 3.2 from 15 g of the compound obtained in the preceding step and 50 ml of a 90% H$_2$SO$_4$ solution. 5.5 g of the expected product are obtained.

C) 1-(Piperazin-1-yl)cyclohexanecarboxamide Dihydrochloride.

This compound is prepared according to the procedure described in step C of Preparation 3.2 from 2.3 g of the compound obtained in the preceding step, 0.3 g of 10% palladium-on-charcoal in 30 ml of 95% EtOH. 1.6 g of the expected product are obtained.

PREPARATION 3.4

N,N-Dimethyl-2-(piperazin-1-yl)isobutyramide Diformate

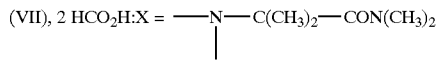

(VII), 2 HCO$_2$H:X = —N—C(CH$_3$)$_2$—CON(CH$_3$)$_2$

A) N,N-Dimethyl-2-(4-benzylpiperazin-1-yl)isobutyramide.

1.44 g of 60% sodium hydride in oil are added portionwise to a mixture of 2.6 g of the compound obtained in step B of Preparation 3.2 (free base) in 50 ml of anhydrous THF. 1.3 ml of methyl iodide are then added dropwise and the mixture is left stirring for 4 hours at RT. The reaction mixture is poured into water, extracted with ether, the organic phase dried over MgSO$_4$ and the solvents evaporated off under vacuum. 1.8 g of the expected product are obtained.

B) N,N-Dimethyl-2-(piperazin-1-yl)isobutyramide diformate.

2 g of ammonium formate and 0.5 g of 5% palladium-on-charcoal are added to a solution of 1.8 g of the compound obtained in the preceding step in 30 ml of MeOH and the mixture is left stirring for 4 hours at RT. The catalyst is filtered off on Celite® and the filtrate is concentrated under vacuum. The residue is taken up in AcOEt, the filtrate formed is drained, washed with AcOEt and dried. 1.2 g of the expected product are obtained.

PREPARATION 3.5

1-(Piperidin-4-yl)cyclohexanecarboxamide Hydrochloride (VII), HCl:X = >CH CONH$_2$ A) 1-(Pyridin-4-yl)cyclohexanecarbonitrile.

A mixture of 3 g of pyridin-4-ylacetonitrile hydrochloride in 50 ml of DMF is cooled to 0° C., 2.6 g of 60% sodium hydride in oil are added in small portions and the mixture is left stirring for 1 hour 30 minutes at RT. The reaction mixture is cooled on an ice bath, 2.7 ml of 1,5-dibromopentane are added dropwise and the mixture is left stirring for 48 hours at RT. The reaction mixture is poured over a saturated NH$_4$Cl solution, extracted with ether, the organic phase washed three times with water, dried over MgSO$_4$ and the solvent evaporated off under vacuum. The residue is chromatographed on H silica gel, eluting with DCM and then with the DCM/MeOH (98/2; v/v) mixture. 2.5 g of the expected product are obtained, m.p.=79° C.

B) 1-(Pyridin-4-yl)cyclohexanecarboxamide Hydrochloride.

A mixture of 2.5 g of the compound obtained in the preceding step and 15 ml of a concentrated H$_2$SO$_4$ solution is heated at 100° C. for 15 minutes. The reaction mixture is cooled to RT, it is poured over ice, alkalinized to pH=14 by addition of a concentrated NaOH solution, the precipitate formed is drained, washed with water and dried. The product obtained is dissolved in acetone, acidified to pH=1 by addition of hydrochloric ether, left stirring for 30 minutes at RT and the precipitate formed is drained. 3 g of the expected product are obtained, m.p.=224° C. (dec.).

C) 1-(Piperidin-4-yl)cyclohexanecarboxamide Hydrochloride.

A mixture of 2.9 g of the compound obtained in the preceding step, 0.5 g of PtO$_2$ and 50 ml of MeOH is hydrogenated for 3 days, at 60° C., at a pressure of 80 bar. The catalyst is filtered off on Celite® and the filtrate is concentrated under vacuum. The residue is taken up in acetonitrile, left stirring for 1 hour at RT and the precipitate formed is drained. 2.7 g of the expected product are obtained, m.p.=235° C.

PREPARATION 3.6

1-(Piperidin-4-yl)cyclopropanecarboxamide Hydrochloride

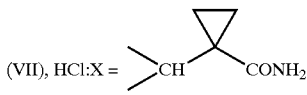

(VII), HCl:X = >CH CONH$_2$

A) 1-(Pyridin-4-yl)cyclopropanecarbonitrile.

3.5 g of pyridin-4-ylacetonitrile and then 2.6 ml of 1,2-dibromoethane are added to a mixture of 2.5 g of sodium amide in 80 ml of DCM and the mixture is left stirring overnight at RT. The reaction mixture is poured into water, extracted with AcOEt, the organic phase washed with water, dried over Na$_2$SO$_4$ and the solvents evaporated off under vacuum. The residue is chromatographed on silica gel, eluting with DCM and then with the DCM/MeOH mixture from (99/1; v/v) to (95/5; v/v). 2.5 g of the expected product are obtained.

B) 1-(Pyridin-4-yl)cyclopropanecarboxamide Hydrochloride.

A mixture of 2.5 g of the compound obtained in the preceding step and 20 ml of a 96% H$_2$SO$_4$ solution is rapidly heated to 100° C. and the mixture is left stirring for 1 hour at 100° C. After cooling to RT, the reaction mixture is poured over ice, neutralized to pH=7 by addition of a 20% NH$_4$OH solution, the precipitate formed is drained, washed with water and dried. The precipitate is dissolved in DCM, the mixture is acidified to pH=1 by addition of hydrochloric ether and the precipitate formed is drained. 1.8 g of the expected product are obtained.

C) 1-(Piperidin-4-yl)cyclopropanecarboxamide Hydrochloride.

A mixture of 1.8 g of the compound obtained in the preceding step and 0.6 g of PtO$_2$ in 50 ml of MeOH is hydrogenated for 15 hours at 80° C. and at a pressure of 100 bar. The catalyst is filtered off on Celite®, the filtrate is concentrated under vacuum to a volume of 5 ml and acetonitrile is added until crystallization is obtained. 1.7 g of the expected product are obtained after draining and then drying.

PREPARATION 3.7

N,N-Dimethyl-2-(piperidin-4-yl)isobutyramide Hydrochloride

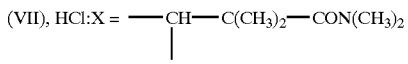

(VII), HCl:X = —CH—C(CH$_3$)$_2$—CON(CH$_3$)$_2$

A) 1-Benzylpiperidine-4-carboxylic Acid Ethyl Ester.

30 g of benzyl bromide are added dropwise to a mixture of 25 g of ethyl isonipecotate and 25 g of K$_2$CO$_3$ in 125 ml of DMF while the temperature of the reaction mixture is maintained between 25 and 30° C. and then the mixture is left stirring for 1 hour at RT. The reaction mixture is poured over 1 litre of ice-cold water, extracted twice with ether, the organic phase washed with water, dried over MgSO$_4$ and the solvent evaporated off under vacuum. The resulting oil obtained is distilled under reduced pressure. 29.2 g of the expected product are obtained, b.p.=120–122° C. at 2.7 Pa.

B) 2-(1-Benzylpiperidin-4-yl)propan-2-ol.

A solution of 24.73 g of the compound obtained in the preceding step in 100 ml of benzene is added dropwise, while the temperature of the medium is maintained between 25 and 30° C., to 200 ml of a 1.5M solution of methyllithium, as a complex with lithium bromide, in ether, and then the mixture is heated under reflux for 48 hours. The reaction mixture is cooled to RT and then it is poured over 400 ml of a saturated NH$_4$Cl solution in water previously cooled on an ice bath. The mixture is extracted three times with ether, the combined organic phases dried over MgSO$_4$ and the solvent concentrated under vacuum. The residue is dissolved in 100 ml of acetone, the mixture is cooled to 10° C., acidified to pH=1 by addition of hydrochloric ether and the precipitate formed is drained and washed with an acetone/ether (50/50; v/v) mixture. 24.5 g of the expected product are obtained in hydrochloride form, m.p.=204° C. To release the base, the hydrochloride is taken up in a concentrated NaOH solution, extracted with ether, dried over MgSO$_4$ and the solvent evaporated off under vacuum. 21 g of the expected product are obtained, m.p.=66° C.

C) 2-(1-Benzylpiperidin-4-yl)-2-methylpropionic Acid.

A mixture of 5.98 g of 95% sulphuric acid and 4.42 g of 30% fuming sulphuric acid in SO$_3$ is cooled to 3° C. and a solution 2 g of the compound obtained in the preceding step in 1.55 g of 100% formic acid is added dropwise while the temperature is maintained below 10° C. The mixture is left stirring for 2 hours at 3–5° C. and then the temperature is allowed to return to RT and the mixture is left overnight at RT. The reaction mixture is poured over ice, adjusted to pH=6.5 by addition of a concentrated NaOH solution and by addition of a concentrated NH$_4$OH solution, extracted three times with DCM, the combined organic phases are dried over MgSO$_4$ and the solvent is concentrated under vacuum. The residue is taken up in acetone, the precipitate drained and dried. 1.22 g of the expected product are obtained, m.p.=195° C.

D) N,N-Dimethyl-2-(1-benzylpiperidin-4-yl)isobutyramide Hydrochloride.

A mixture of 1.2 g of the compound obtained in the preceding step, 0.8 ml of triethylamine, 2.8 ml of a 2 M dimethylamine solution in THF and 2.5 g of BOP in 20 ml of DCM is left stirring for 1 hour at RT. The reaction mixture is concentrated under vacuum, the residue taken up in ether, the organic phase washed with water, with a 1N NaOH solution, with a saturated NaCl solution, dried over MgSO$_4$ and the solvent concentrated under vacuum. The residue is chromatographed on H silica gel, eluting with DCM and then with the gradient of the DCM/MeOH mixture from (99/1; v/v) to (95/5; v/v). The product obtained is dissolved in acetone, the mixture is acidified to pH=1 by addition of hydrochloric ether, the precipitate formed is drained and dried. 0.8 g of the expected product is obtained, m.p.=229° C.

E) N,N-Dimethyl-2-(piperidin-4-yl)isobutyramide Hydrochloride.

A mixture of 0.8 g of the compound obtained in the preceding step and 0.2 g of 10% palladium-on-charcoal in 20 ml of MeOH is hydrogenated overnight at atmospheric pressure and at RT. The catalyst is filtered off on Celite® and the filtrate is concentrated under vacuum. The residue is dissolved in acetonitrile, ether is added, the precipitate formed is drained and dried. 0.51 g of the expected product is obtained, m.p.=258° C.

PREPARATION 3.8

2-Methyl-1-(morpholin-4-yl)-2-(piperidin-4-yl)propan-1-one hydrochloride

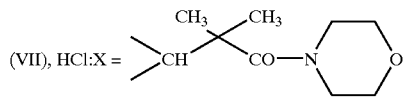

A) 2-(1-Benzylpiperidin-4-yl)-2-methyl-1-(morpholin-4-yl)propan-1-one Hydrochloride.

A mixture of 1 g of the compound obtained in step C of Preparation 3.7 and 1.2 ml of thionyl chloride in 20 ml of 1,2-dichloroethane is heated at 80° C. for 3 hours. The reaction mixture is concentrated under vacuum, the acid chloride thus obtained is dissolved in 20 ml of DCM, this solution is added to a mixture of 0.7 g of morpholine, 1.6 ml of triethylamine in 20 ml of DCM previously cooled to 0° C. and the mixture is left stirring for 24 hours at RT. The reaction mixture is concentrated under vacuum, the residue extracted with ether, the organic phase washed with a 1N NaOH solution, with water, dried over MgSO$_4$ and the solvent evaporated off under vacuum. The product obtained is dissolved in acetone, the mixture is acidified to pH=1 by addition of hydrochloric ether, the precipitate formed is drained and dried. 0.7 g of the expected product is obtained.

B) 2-Methyl-1-(morpholin-4-yl)-2-(piperidin-4-yl)propan-1-one Hydrochloride.

A mixture of 0.7 g of the compound obtained in the preceding step, 0.7 g of ammonium formate and 0.2 g of 10% palladium-on-charcoal in 10 ml of MeOH is left stirring for 4 hours at RT. The catalyst is filtered off on Celite® and the filtrate is concentrated under vacuum. The residue is dissolved in acetonitrile, ether is added, the precipitate formed is drained and dried. 0.46 g of the expected product is obtained, m.p.=225° C.

EXAMPLE 1

2-[2-(4-Cyclohexylpiperazin-1-yl)ethyl]-2-(3,4-dichlorophenyl)-4-[2-(3,5-dimethylphenyl)acetyl]morpholine dihydrochloride, monohydrate, (−) isomer.

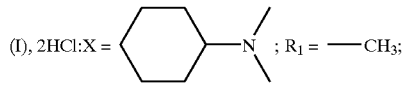

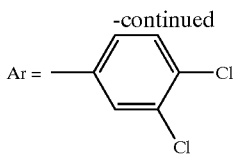

A) 2-[2-(Benzoyloxy)ethyl]-2-(3,4-dichlorophenyl)-4-[2-(3,5-dimethylphenyl)acetyl]morpholine, Single Isomer.

A mixture of 2.2 g of the compound obtained in Preparation 1.1, 1.48 g of triethylamine and 0.96 g of 3,5-dimethylphenylacetic acid in 40 ml of DCM is cooled on an ice bath, 2.85 g of BOP are added and the mixture is left stirring for 3 hours while the temperature is allowed to return to RT. The reaction mixture is concentrated under vacuum, the residue extracted with AcOEt, the organic phase washed with water, with a 10% Na$_2$CO$_3$ solution, with water, with a saturated NaCl solution, dried over Na$_2$SO$_4$ and the solvent evaporated off under vacuum. The residue is chromatographed on H silica gel, eluting with the DCM/MeOH (100/0,5; v/v) mixture. 2.4 g of the expected product are obtained in the form of an oil.

B) 2-(3,4-Dichlorophenyl)-2-(2-hydroxyethyl)-4-[2(3,5-dimethylphenyl)acetyl]morpholine, Single Isomer.

A mixture of 2.4 g of the compound obtained in the preceding step and 1.7 ml of a 30% aqueous NaOH solution, in 30 ml of MeOH, is left stirring for 30 minutes at RT. The reaction mixture is concentrated under vacuum, the residue taken up in water, extracted with AcOEt, the organic phase washed with water, with a saturated NaCl solution, dried over Na$_2$SO$_4$ and the solvent evaporated off under vaccum. 1.92 g of the expected product are obtained in the form of an oil.

C) 2-(3,4-Dichlorophenyl)-2-[2(methanesulphonyloxy)ethyl]-4-[2-(3,5-dimethylphenyl)-acetyl]morpholine, Single Isomer.

A solution of 1.92 g of the compound obtained in the preceding step and 0.94 ml of triethylamine in 30 ml of DCM is cooled on an ice bath and a solution of 0.57 g of methanesulphonyl chloride in 10 ml of DCM is added dropwise and the mixture is left stirring for 5 minutes. The reaction mixture is concentrated under vacuum, the residue taken up in water, extracted with AcOEt, the organic phase washed with water, with a saturated NaCl solution, dried over Na$_2$SO$_4$ and the solvent evaporated off under vacuum. 2.22 g of the expected product are obtained in the form of an oil.

D) 2-[2-(4-Cyclohexylpiperazin-1-yl)ethyl]-2-(3,4-dichlorophenyl)-4-[2-(3,5-dimethylphenyl)-acetyl]morpholine Dihydrochloride, Monohydrate, (−) Isomer.

A mixture of 1.1 g of the compound obtained in the preceding step, 0.56 g of 1-cyclohexylpiperazine and 0.61 g of K$_2$CO$_3$ in 2 ml of DMF is heated at 80° C. for 3 hours. After cooling to RT, ice-cold water is added to the reaction mixture, the mixture is extracted with AcOEt, the organic phase washed with water, with a saturated NaCl solution, dried over Na$_2$SO$_4$ and the solvent evaporated off under vacuum. The residue is chromatographed on H silica gel, eluting with the DCM/MeOH (100/3; v/v) mixture. The product obtained is dissolved in DCM, hydrochloric ether is added to pH=1 and the mixture is concentrated under vacuum. 0.51 g of the expected product is obtained after concretion in the DCM/pentane mixture.

$\alpha_D^{20}$=28.7° (c=1; MeOH). $^1$H NMR: δ (ppm): 0.7 to 2.45: m: 18H; 2.5 to 4.65: m: 19H; 6.4 to 7.8: m: 6H; 11.8: s: 2H.

EXAMPLE 2

2-[2-(4-Cyclohexylpiperazin-1-yl)ethyl]-2-(3,4-dichlorophenyl)-4-[2-(3,5-dichlorophenyl)acetyl]morpholine Dihydrochloride, Hemihydrate, (+) Isomer

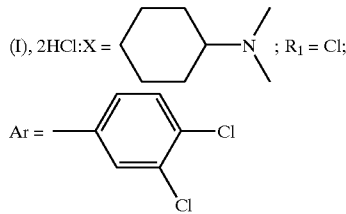

(I), 2HCl:X = ; $R_1$ = Cl;

A) 2-[2-(Benzoyloxy)ethyl]-2-(3,4-dichlorophenyl)-4-[2-(3,5-dichlorophenyl)acetyl]morpholine, Single Isomer.

This compound is prepared according to the procedure described in step A of EXAMPLE 1 from 1.92 g of the compound obtained in Preparation 1.1, 1.27 g of triethylamine, 1.04 g of 3,5-dichlorophenylacetic acid, 35 ml of DCM and 2.46 g of BOP. 2.2 g of the expected product are obtained in the form of an oil.

B) 2-(3,4-Dichlorophenyl)-4-[2-(3,5-dichlorophenyl)acetyl]-2-(2-hydroxyethyl)morpholine, Single Isomer.

This compound is prepared according to the procedure described in step B of EXAMPLE 1 from 2.2 g of the compound obtained in the preceding step, 1.5 ml of a 30% aqueous NaOH solution and 30 ml of MeOH. 1.8 g of the expected product are obtained in the form of an oil.

C) 2-(3,4-Dichlorophenyl)-4-[2-(3,5-dichlorophenyl)acetyl]-2-[2-(methane-sulphonyloxy)ethyl]morpholine, Single Isomer.

This compound is prepared according to the procedure described in step C of EXAMPLE 1 from 1.8 g of the compound obtained in the preceding step, 0.59 g of triethylamine, 30 ml of DCM and 0.49 g of methanesulphonyl chloride in 10 ml of DCM. 2 g of the expected product are obtained in the form of an oil.

D) 2-[2-(4-Cyclohexylpiperazin-1-yl)ethyl]-2-(3,4-dichlorophenyl)-4-[2-(3,5-dichlorophenyl)acetyl]morpholine Dihydrochloride, Hemihydrate, (+) Isomer.

This compound is prepared according to the procedure described in step D of EXAMPLE 1 from 1 g of the compound obtained in the preceding step, 0.45 g of 1-cyclohexylpiperazine, 0.51 g of $K_2CO_3$ and 2 ml of DMF. 0.54 g of the expected product is obtained.

$\alpha_D^{20}$=+1.2° (c=1; MeOH). $^1$H NMR: δ (ppm) 0.8 to 2.5 m: 12H; 2.55 to 4.4: m: 19H; 7.0 to 8.0: m: 6H; 11.6: s: 2H.

EXAMPLE 3

2-[2-(4-Cyclohexylpiperazin-1-yl)ethyl]-2-(3,4-dichlorophenyl)-4-[2-[3,5-bis(trifluoromethyl)phenyl]acetyl]morpholine Dihydrochloride, Hemihydrate, (+) Isomer.

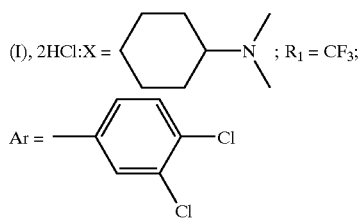

(I), 2HCl:X = ; $R_1$ = $CF_3$;

A) 2-[2-(Benzoyloxy)ethyl]-2-(3,4-dichlorophenyl)-4-[2-[3,5-bis(trifluoromethyl)phenyl]acetyl]morpholine, Single Isomer.

This compound is prepared according to the procedure described in step A of EXAMPLE 1 from 2.23 g of the compound obtained in Preparation 1.1, 1.48 g of triethylamine, 1.59 g of 3,5-bis(trifluoromethyl)phenylacetic acid, 40 ml of DCM and 2.85 g of BOP. 2.4 g of the expected product are obtained in the form of an oil.

B) 2-(3,4-Dichlorophenyl)-4-[2-[3,5-bis(trifluoromethyl)phenyl]acetyl]-2-(2-hydroxyethyl)morpholine, Single Isomer.

This compound is prepared according to the procedure described in step B of EXAMPLE 1 from 2.4 g of the compound obtained in the preceding step, 1.4 ml of a 30% aqueous NaOH solution and 30 ml of MeOH. 2 g of the expected product are obtained in the form of an oil.

C) 2-(3,4-Dichlorophenyl)-4-[2-[3,5-bis(trifluoromethyl)phenyl]acetyl]-2-[2-(methanesulphonyloxy)ethyl]morpholine, Single Isomer.

This compound is prepared according to the procedure described in step C of EXAMPLE 1 from 2 g of the compound obtained in the preceding step, 0.57 g of triethylamine, 30 ml of DCM and 0.47 g of methanesulphonyl chloride in 10 ml of DCM. 2.29 g of the expected product are obtained in the form of an oil.

D) 2-[2-(4-Cyclohexylpiperazin-1-yl)ethyl]-2-(3,4-dichlorophenyl)-4-[2-[3,5-bis(trifluoromethyl)phenyl]acetyl]morpholine Dihydrochloride, Hemihydrate, (+) Isomer.

A mixture of 1 g of the compound obtained in the preceding step, 0.29 g of 1-cyclohexylpiperazine and 0.71 g of $K_2CO_3$ in 3 ml of DMF is heated at 80–100° C. for 2 hours. After cooling to RT, the reaction mixture is poured into water, extracted with AcOEt, the organic phase washed with water, dried over $Na_2SO_4$ and the solvent evaporated off under vacuum. The residue is chromatographed on H silica gel, eluting with the gradient of the DCM/MeOH mixture from (100/2; v/v) to (100/5; v/v). The product obtained is dissolved in DCM, hydrochloric ether is added to pH=1 and the mixture is concentrated under vacuum. 0.6 g of the expected product is obtained after concretion in the DCM/pentane mixture.

$\alpha_D^{20}$=+23.4° (c=0.5; MeOH). $^1$H NMR: δ (ppm): 0.8 to 2.6 m: 12H; 2.6 to 4.3: m: 19H; 7.1 to 8.0: m: 6H; 11.8: m: 2H.

EXAMPLE 4

2-[2-[4-(1-Carbamoyl-1-methylethyl)piperidin-1-yl]ethyl]-2-(3,4-dichlorophenyl)-4-[2-(3,5-dimethylphenyl)acetyl]morpholine Hydrochloride, Sesquihydrate, (−) Isomer.

(I), HCl:X = $H_2NCO$—$C(CH_3)_2$—CH——; $R_1$ = ——$CH_3$;

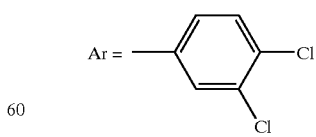

Ar =

A) 2-(3,4-Dichlorophenyl)-2-(formylmethyl)-4-[2-(3,5-dimethylphenyl)acetyl]morpholine, Single Isomer.

A solution of 0.63 ml of oxalyl chloride in 20 ml of DCM is cooled to −60° C. under a nitrogen atmosphere, a solution of 1.3 ml of DMSO in 20 ml of DCM, and then a solution of 2.55 g of the compound obtained in step B of Example 1 and 1.84 ml of DMSO in 20 ml of DCM are added dropwise. The mixture is left stirring for 30 minutes at −60° C., the temperature is allowed to rise to −50° C., 5.2 ml of triethylamine are added and the mixture is left stirring while the temperature is allowed to rise to RT. The reaction mixture is washed with a 2N HCl solution, with water, with a saturated NaHCO$_3$ solution, with water, the organic phase dried over MgSO$_4$ and the solvent evaporated off under vacuum. 2.38 g of the expected product are obtained.

B) 2-[2-[4-(1-Carbamoyl-1-methylethyl)piperidin-1-yl]ethyl]-2-(3,4-dichlorophenyl)-4-[2-(3,5-dimethylphenyl)acetyl]morpholine Hydrochloride, Sesquihydrate, (−) Isomer.

0.26 g of the compound obtained in Preparation 3.1 (free base) and then 0.74 g of sodium triacetoxyborohydride and 8 drops of acetic acid are added at RT and under a nitrogen atmosphere to a solution of 0.64 g of the compound obtained in the preceding step in 30 ml of DCM and the mixture is left stirring overnight at RT. The reaction mixture is alkalinized to pH=8 by addition of a saturated NaHCO$_3$ solution, extracted with DCM, the organic phase washed three times with water, dried over MgSO$_4$ and the solvent evaporated off under vacuum. The residue is chromatographed on H silica gel, eluting with the gradient of the DCM/MeOH mixture from (100/1; v/v) up to (100/5; v/v). The product obtained is dissolved in DCM, hydrochloric ether is added to pH=1, the precipitate formed is drained and dried. 0.631 g of the expected product is obtained.

$\alpha_D^{20}$=+23.8° (c=0.5; MeOH). $^1$H NMR: δ (ppm): 0.8 to 1.2: se: 6H; 1.2 to 2.0: m: 6H; 2.0 to 4.8: m: 21H; 6.6 to 8.8: m: 8H; 10.2: se: 1H.

EXAMPLE 5

2-[2-[4-(1-Carbamoyl-1-methylethyl)piperidin-1-yl]ethyl]-2-(3,4-dichlorophenyl)-4-[2-(3,5-diethylphenyl)acetyl]morpholine Hydrochloride, Hemihydrate, (−) Isomer.

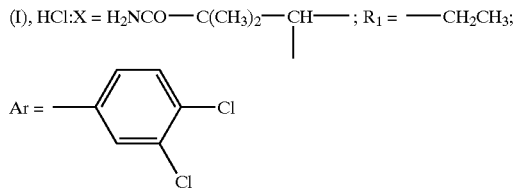

A) 2-[2-(Benzoyloxy)ethyl]-2-(3,4-dichlorophenyl)-4-[2-(3,5-diethylphenyl)acetyl]morpholine, Single Isomer.

A solution of 2.27 g of the compound obtained in Preparation 1.1 in 25 ml of DCM is cooled to 0° C., 1.15 g of the compound obtained in Preparation 2.2, 0.72 g of triethylamine and then 3.17 g of BOP are added and the mixture is left stirring for 1 hour. The reaction mixture is extracted with DCM, the organic phase washed with water, with a buffer solution pH=2, with water, with a 10% Na$_2$CO$_3$ solution, with water, dried over Na$_2$SO$_4$ and the solvent evaporated off under vacuum. The residue is chromatographed on H silica gel, eluting with DCM and then with the DCM/MeOH (100/1 v/v) mixture. 3.1 g of the expected product are obtained.

B) 2-(3,4-Dichlorophenyl)-2-(2-hydroxyethyl)-4-[2(3,5-diethylphenyl)acetyl]morpholine, Single Isomer.

A mixture of 3.1 g of the compound obtained in the preceding step and 1.5 ml of a 30% aqueous NaOH solution, in 130 ml of MeOH, is left stirring for 1 hour at RT. The reaction mixture is concentrated under vacuum, the residue extracted with an AcOEt/ether (50/50; v/v) mixture, the organic phase washed three times with water, dried over Na$_2$SO$_4$ and the solvent evaporated off under vacuum. The residue is chromatographed on H silica gel, eluting with DCM and then with the DCM/MeOH (100/2; v/v) mixture. 2 g of the expected product are obtained.

C) 2-(3,4-Dichlorophenyl)-2-(formylmethyl)-4-[2-(3,5-diethylphenyl)acetyl]morpholine, Single Isomer.

This compound is prepared according to the procedure described in step A of Example 4 from 0.67 g of oxalyl chloride in 20 ml of DCM, 1.0 g of DMSO in 10 ml of DCM, 2.0 g of the compound obtained in the preceding step and 1.44 g of DMSO in 20 ml of DCM and 2.9 g of triethylamine. 1.95 g of the expected product are obtained.

D) 2-[2-[4-(1-Carbamoyl-1-methylethyl)piperidin-1-yl]ethyl]-2-(3,4-dichlorophenyl)-4-[2-(3,5-diethylphenyl)acetyl]morpholine Hydrochloride, Hemihydrate, (−) Isomer.

This compound is prepared according to the procedure described in step B of Example 4 from 0.58 g of the compound obtained in the preceding step in 50 ml of DCM, 0.23 g of the compound obtained in Preparation 3.1 (free base), 0.58 g of sodium triacetoxyborohydride and 8 drops of acetic acid. 0.4 g of the expected product is obtained.

$\alpha_D^{20}$=−23.4° (c=0.5; MeOH) $^1$H NMR: δ (ppm) 0.6 to 1.8: m: 18H; 1.8 to 4.8: m: 19H; 6.4 to 8.0: m: 8H; 9.8 to 10.2: se: 1H.

EXAMPLE 6

2-[2-(4-(1-Carbamoylcyclohexyl)piperidin-1-yl]ethyl]-2-(3,4-dichlorophenyl)-4-[2-[3,5-bis(trifluoromethyl)phenyl]acetyl]morpholine Hydrochloride, (+) Isomer.

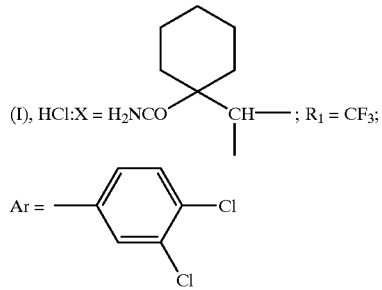

A) 2-(3,4-Dichlorophenyl)-2-(formylmethyl)-4-[2-[3,5-bis(trifluoromethyl)phenyl]acetyl]morpholine, Single Isomer.

This compound is prepared according to the procedure described in step A of Example 4 from 0.62 ml of oxalyl chloride in 15 ml of DCM, 1.26 ml of DMSO in 15 ml of DCM, 3.15 g of the compound obtained in step B of Example 3 and 1.81 ml of DMSO in 15 ml of DCM and 5.12 ml of triethylamine. 3.13 g of the expected product are obtained.

B) 2-[2-[4-(1-Carbamoylcyclohexyl)piperidin-1-yl]ethyl]-2-(3,4-dichlorophenyl)-4-[2-[3,5-bis(trifluoromethyl)phenyl]acetyl]morpholine Hydrochloride, (+) Isomer.

This compound is prepared according to the procedure described in step B of Example 4 from 0.5 g of the compound obtained in the preceding step in 20 ml of DCM, 0.198 g of the compound obtained in Preparation 3.5 (free base), 0.46 g of sodium triacetoxyborohydride and 7 drops of acetic acid. 0.467 g of the expected product is obtained.

$\alpha_D^{20}$=+28.8° (c=0.5; MeOH). $^1$H NMR: δ (ppm) 0.6 to 1.9: m: 12H; 1.9 to 4.5: m: 18H; 6.8 to 8.2m: 8H; 9.8 to 10.4: 2s: 2H.

By carrying out the procedure according to the procedures described in the preceding Examples, the compounds according to the invention which are assembled in Table I below are prepared.

(a) This compound is prepared according to the procedure described in step B of Example 4 from the compound obtained in step A of Example 4 and from the compound obtained in Preparation 3.2 in the form of a free base.

(b) This compound is prepared according to the procedure described in step B of Example 4 from the compound obtained in step A of Example 4 and from the compound obtained in Preparation 3.3 in the form of a free base.

(c) This compound is prepared according to the procedure described in step D of Example 5 from the compound obtained in step C of Example 5 and from the compound obtained in Preparation 3.2 in the form of a free base.

(d) This compound is prepared according to the procedure described in step D of Example 5 from the compound obtained in step C of Example 5 and from the compound obtained in Preparation 3.4 in the form of a free base.

(e) This compound is prepared according to the procedure described in step D of Example 5 from the compound obtained in step C of Example 5 and from 1-cyclohexylpiperazine.

(f) This compound is prepared according to the procedure described in step B of Example 4 from the compound obtained in step A of Example 4 and from the compound obtained in Preparation 3.6 in the form of a free base.

(g) This compound is prepared according to the procedure described in step B of Example 4 from the compound obtained in step A of Example 6 and from the compound obtained in Preparation 3.2 in the form of a free base.

EXAMPLE 7

$^1$H NMR: δ (ppm): 1.6: se: 6H; 2.0 to 2.4: m: 8H; 2.5 to 5.0: m: 18H; 6.6 to 8.0: m: 10H.

EXAMPLE 8

$^1$H NMR: δ (ppm): 0.8 to 2.4: m: 18H; 2.6 to 4.8 m: 18H; 6.4 to 8.2: m: 8H.

EXAMPLE 9

$^1$H NMR: δ (ppm): 0.8 to 1.2: 2t: 6H; 1.4: se: 6H; 2.0 to 5.0: m: 24H; 6.4 to 8.0: m: 6H.

EXAMPLE 10

$^1$H NMR: δ (ppm): 0.6 to 1.8: m: 12H; 2.0 to 4.8: m: 32H; 6.4 to 8.0: m: 6H; 10.6 to 11: se: 2H.

EXAMPLE 11

$^1$H NMR: δ (ppm): 0.9 to 2.7: m: 22H; 2.7 to 4.8: m: 19H; 6.4 to 7.8: m: 6H; 11.75: s: 1H.

EXAMPLE 12

$^1$H NMR: δ (ppm): 0.4 to 1.0: 2 mt: 4H; 1.3 to 2.5: m: 13H; 2.55 to 4.5: m: 14H; 6.4 to 7.8: m 8H; 10.1: s: 1H.

EXAMPLE 13

$^1$H NMR: δ (ppm): 1.4: se: 6H; 2.15 to 4.4: m: 20H; 7.2 to 8.2: m: 8H.

EXAMPLE 14

2-[2-[4-(1-Carbamoyl-1-methylethyl)piperidin-1-yl]ethyl]-2-(3,4-dichlorophenyl)-4-[2-(3,5-dichlorophenyl)acetyl]morpholine hydrochloride, hemihydrate, (+) isomer.

(I), HCl:X = H$_2$NCO—C(CH$_3$)$_2$—CH—; R$_1$ = Cl;

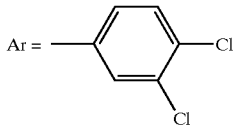

A) 2-(3,4-Dichlorophenyl)-2-(formylmethyl)-4-[2-(3,5-dichlorophenyl)acetyl]morpholine, Single Isomer.

This compound is prepared according to the procedure described in step A of Example 4 from 0.715 g of oxalyl chloride in 15 ml of DCM, 1.08 g of DMSO in 15 ml of DCM, 2.14 g of the compound obtained in step B of Example 2 and 1.55 g of DMSO in 15 ml of DCM and 2.89 g of triethylamine. 2.13 g of the expected product are obtained.

B) 2-[2-[4-(1-Carbamoyl-1-methylethyl)piperidin-1-yl]ethyl]-2-(3,4-dichlorophenyl)-4-[2-(3,5-dichlorophenyl)acetyl]morpholine Hydrochloride, Hemihydrate, (+) Isomer.

This compound is prepared according to the procedure described in step B of Example 4 from 0.47 g of the compound obtained in the preceding step in 20 ml of DCM, 0.21 g of the compound obtained in Preparation 3.1 (free base), 0.5 g of sodium triacetoxyborohydride and 8 drops of acetic acid. 0.428 g of the expected product is obtained.

α$_D^{20}$=+4.8° (c=0.5; MeOH) $^1$H NMR: δ (ppm):0.9: s: 6H; 1.3 to 2.5: m: 7H; 2.5 to 4.2: m: 14H; 6.6 to 7.8: m: 8H; 10.1: 2s: 1H.

EXAMPLE 15

2-[2-[4-(1-Carbamoyl-1-methylethyl)piperidin-1-yl]ethyl]-2-(3,4-dichlorophenyl)-4-[2-[3,5-bis(trifluoromethyl)phenyl]acetyl]morpholine hydrochloride, monohydrate, (+) isomer.

(I), HCl:X = H$_2$NCO—C(CH$_3$)$_2$—CH—; R$_1$ = CF$_3$;

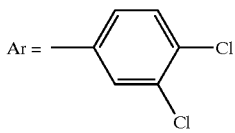

A mixture of 0.3 g of the compound obtained in Preparation 3.1 and 0.6 g of K$_2$CO$_3$ in 10 ml of acetonitrile is heated under reflux for 3 hours. The insoluble matter is filtered off and the filtrate is concentrated under vacuum. The product of Preparation 3.1 is dissolved in the form of a free base thus obtained in 20 ml of DCM, 0.77 g of the compound obtained in step A of Example 6 is added, followed by 0.62 g of sodium triacetoxyborohydride and 8 drops of acetic acid and the mixture is left stirring overnight at RT and under a nitrogen atmosphere. The reaction mixture is alkalinized to pH=8 by addition of a 10% Na$_2$CO$_3$ solution, extracted with DCM, the organic phase washed 3 times with water, with a saturated NaCl solution, dried over MgSO$_4$ and the solvent evaporated off under vacuum. The residue is chromatographed on H silica gel, eluting with DCM, and then with the DCM/MeOH (95/5; v/v) mixture.

45

The product obtained is dissolved in AcOEt, hydrochloric ether is added to pH=1, the precipitate formed is drained and dried. 0.5 g of the expected product is obtained.

$\alpha_D^{20}$=+29° (c=0.5; MeOH) $^1$H NMR: δ (ppm): 1.0: s: 6H; 1.4 to 2.5: m: 6H; 2.5 to 4.4: m: 15H; 6.8 to 7.2: 2s: 2H; 7.3 to 8.1: m: 6H; 9.7 to 10.15: 2s: 1H.

EXAMPLE 16

2-[2-[4-(1-Carbamoyl-1-methylethyl)piperazin-1-yl]ethyl]-2-(3,4-dichlorophenyl)-4-[2-(3,5-diisopropylphenyl)acetyl]morpholine dihydrochloride, monohydrate, (−) isomer.

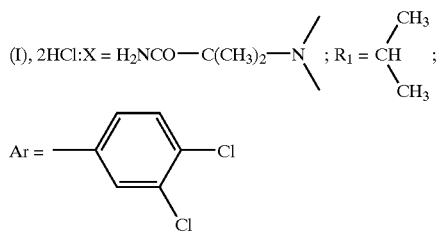

A) 2-(3,4-Dichlorophenyl)-2-(2-hydroxyethyl)-4-[2-(3,5-diisopropylphenyl)acetyl]morpholine, Single Isomer.

A mixture of 1.78 g of the compound obtained in Preparation 1.2, 0.8 g of triethylamine and 1.4 g of 3,5-diisopropylphenylacetic acid in 40 ml of DCM is cooled to 0° C., 2.85 g of BOP are added and the mixture is left stirring for 30 minutes at RT. The reaction mixture is concentrated under vacuum, the residue extracted with ether, the organic phase washed with water, with a buffer solution pH=2, with water, with a 1N NaOH solution, with water, dried over Na$_2$SO$_4$ and the solvent evaporated off under vacuum. The residue is chromatographed on H silica gel, eluting with the gradient of the DCM/MeOH mixture from (100/1; v/v) to (100/3; v/v). 1.2 g of the expected product are obtained.

B) 2-(3,4-Dichlorophenyl)-2-(formylmethyl)-4-[2-(3,5-diisopropylphenyl)acetyl]morpholine, Single Isomer.

This compound is prepared according to the procedure described in step A of Example 4 from 0.4 g of oxalyl chloride in 20 ml of DCM, 0.6 g of DMSO in 10 ml of DCM, 1.2 g of the compound obtained in the preceding step and 0.8 g of DMSO in 20 ml of DCM and 1.64 g of triethylamine. 1.1 g of the expected product are obtained.

C) 2-[2-[4-(1-Carbamoyl-1-methylethyl)piperazin-1-yl]ethyl]-2-(3,4-dichlorophenyl)-4-[2-(3,5-diisopropylphenyl)acetyl]morpholine Dihydrochloride, Monohydrate, (−) Isomer.

This compound is prepared according to the procedure described in step B of Example 4 from 0.45 g of the compound obtained in the preceding step in 50 ml of DCM, 0.2 g of the compound obtained in Preparation 3.2 in the form of a free base, 0.4 g of sodium triacetoxyborohydride and 8 drops of acetic acid. 0.3 g of the expected product are obtained.

$\alpha_D^{20}$=+18.4° (c=0.25; MeOH) $^1$H NMR: δ (ppm) 0.8 to 1.7: m: 18H; 2.2: mt: 2H; 2.5 to 4.7: m: 18H; 6.4 to 8.0 m: 8H.

46

What is claimed is:
1. A compound of formula I:

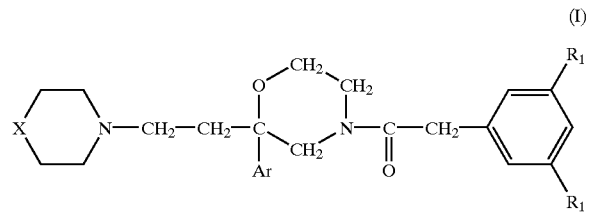

(I)

in which:
Ar represents a phenyl monosubstituted or disubstituted with a halogen atom or a (C$_1$–C$_3$)alkyl;
X represents a group

or a group

R$_1$ represents a chlorine atom, a bromine atom, a (C$_1$–C$_3$) alkyl or a trifluoromethyl;
R$_2$ represents a (C$_1$–C$_6$)alkyl; a (C$_3$–C$_6$)cycloalkyl or a group —CR$_5$CONR$_6$R$_7$;
R$_3$ represents a group —CR$_4$R$_5$CONR$_6$R$_7$;
R$_4$ and R$_5$ are the same and represent a methyl, an ethyl, an n-propyl or an n-butyl;
or R$_4$ and R$_5$, together with the carbon atom to which they are attached, constitute a (C$_3$–C$_6$)cycloalkyl;
R$_6$ and R$_7$ each independently represent a hydrogen or a (C$_1$–C$_3$)alkyl;
or R$_6$ and R$_7$, together with the nitrogen atom to which they are attached, constitute a heterocyclic radical chosen from 1-azetidinyl, 1-pyrrolidinyl, 1-piperidinyl, 4-morpholinyl, 4-thiomorpholinyl and perhydro-1-azepinyl; or a salt thereof with an inorganic or organic acid or a solvate or hydrate thereof.

2. A compound according to claim 1, in which Ar represents a 3,4-dichlorophenyl.

3. A compound according to claim 1, in which the substituents R$_1$ represent a chlorine atom, a methyl, an ethyl, an isopropyl or a trifluoromethyl.

4. A compound according to claim 1, in which X represents a group

in which R$_2$ represents a (C$_1$–C$_6$) alkyl or a (C$_3$–C$_6$) cycloalkyl.

5. A compound according to claim 4, in which R$_2$ represents a cyclopentyl or a cyclohexyl.

6. A compound according to claim 1, in which X represents a group

in which $R_2$ represents a group $-CR_4R_5CONR_6R_7$.

7. A compound according to claim 6, in which $R_4$ and $R_5$ each represent a methyl or, together with the carbon atom to which they are attached, constitute a cyclohexyl.

8. A compound according to claim 6, in which $R_6$ and $R_7$ are similar and represent hydrogen or a methyl.

9. A compound according to claim 1, in which X represents a group

in which $R_3$ represents a group $-CR_4R_5CONR_6R_7$.

10. A compound according to claim 9, in which $R_4$ and $R_5$ each represent a methyl or alternatively, together with the carbon atom to which they are attached, constitute a cyclohexyl or a cyclopropyl.

11. A compound according to claim 9, in which $R_6$ and $R_7$ are the same and represent hydrogen or a methyl.

12. A compound according to claim 1 of formula I':

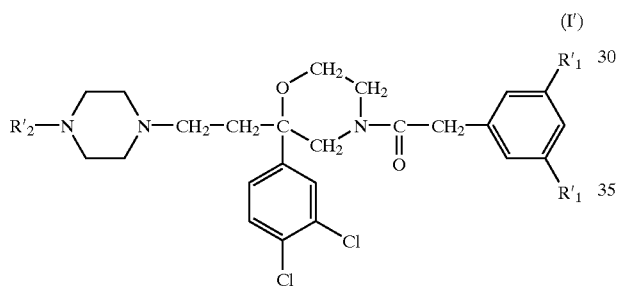

in which:
  $R'_1$ represents a chlorine atom, a methyl, an ethyl, an isopropyl or a trifluoromethyl;
  $R'_2$ represents a cyclopentyl or a cyclohexyl;
or a salt thereof with an inorganic or organic acid or a solvate or hydrate thereof.

13. A compound according to claim 1 of formula I":

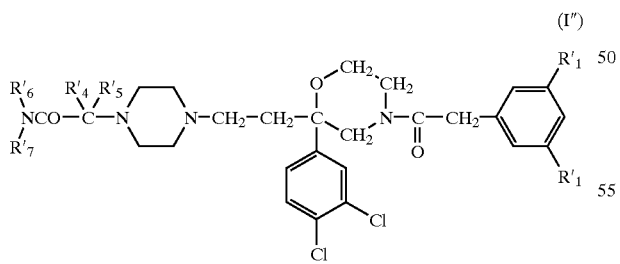

in which:
  $R'_1$ represents a chlorine atom, a methyl, an ethyl, an isopropyl or a trifluoromethyl;
  $R'_4$ and $R'_5$ each represent a methyl or, together with the carbon atom to which they are attached, constitute a cyclohexyl;
  $R'_6$ and $R'_7$ are the same and represent hydrogen or a methyl;

or a salt thereof with an inorganic or organic acid or a solvate or hydrate thereof.

14. A compound according to claim 1 of formula I''':

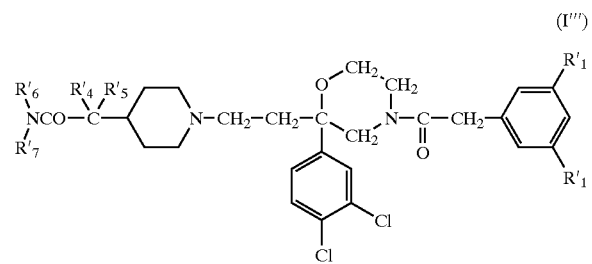

in which:
  $R'_1$ represents a chlorine atom, a methyl, an ethyl, an isopropyl or a trifluoromethyl;
  $R'_4$ and $R'_5$ each represent a methyl or, together with the carbon atom to which they are attached, constitute a cyclohexyl or a cyclopropyl;
  $R'_6$ and $R'_7$ are the same and represent hydrogen or a methyl;

or a salt thereof with an inorganic or organic acid or a solvate or hydrate thereof.

15. A compound according to claim 1 in optically pure form.

16. 2-[2-(4-Cyclohexylpiperazin-1-yl)ethyl]-2-(3,4-dichlorophenyl)-4-[2-[3,5-bis(trifluoromethyl)phenyl]acetyl]morpholine, (+) isomer or a salt, a solvate or a hydrate thereof.

17. 2-[2-[4-(1-Carbamoylcyclohexyl)piperidin-1-yl]ethyl]-2-(3,4-dichlorophenyl)-4-[2-[3,5-bis(trifluoromethyl)phenyl]acetyl]morpholine, (+) isomer or a salt, a solvate or a hydrate thereof.

18. 2-[2-[4-(1-Carbamoyl-1-methylethyl)piperazin-1-yl]ethyl]-2-(3,4-dichlorophenyl)-4-[2-[3,5-bis(trifluoromethyl)phenyl]acetyl]morpholine, (+) isomer or a salt, a solvate or a hydrate thereof.

19. 2-[2-[4-(1-Carbamoyl-1-methylethyl)piperidin-1-yl]ethyl]-2-(3,4-dichlorophenyl)-4-[2-[3,5-bis(trifluoromethyl)phenyl]acetyl]morpholine, (+) isomer or a salt, a solvate or a hydrate thereof.

20. A process for preparing a compound according to claim 1 wherein:

1a) a compound of formula:

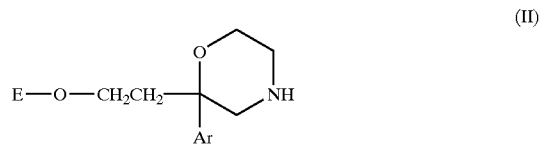

in which Ar is as defined in claim 1 and E represents hydrogen or an O-protecting group, is reacted with a functional derivative of an acid of formula:

(III)

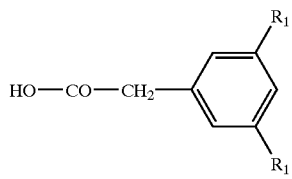

in which $R_1$ is as defined in claim 1, to give a compound of formula:

(IV)

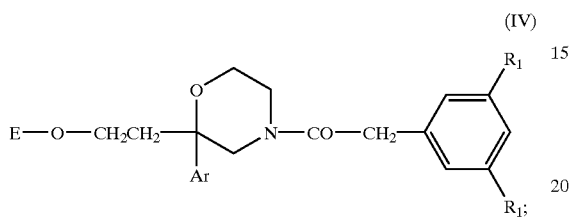

2a) optionally, when E represents a protecting group, it is removed by the action of an acid or a base, to give the alcohol of formula:

(IV, E = H)

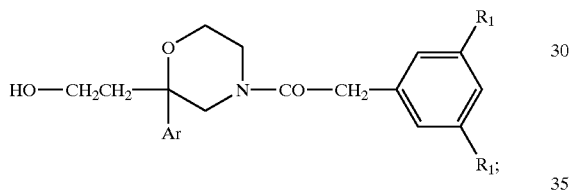

3a) the alcohol obtained in step 1a) or in step 2a) of formula (IV, E=H) is treated with a compound of formula:

$$Y-SO_2-Cl \qquad (V)$$

in which Y represents a methyl, phenyl, tolyl or trifluoromethyl group, to give a compound of formula:

(VI)

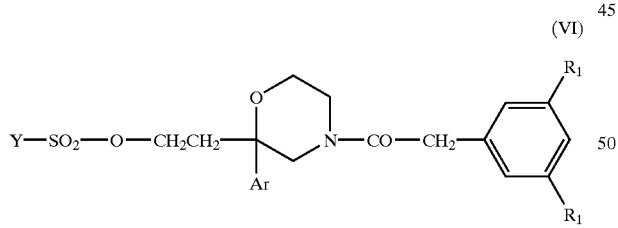

4a) the compound of formula (VI) is reacted with a compound of formula:

(VII)

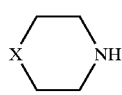

in which X is as defined in claim 1;

5a) and, optionally, the compound thus obtained is converted into a salt thereof with an inorganic or organic acid.

21. A Process for preparing a compound according to claim 1 wherein:

1b) the compound of formula:

(II)

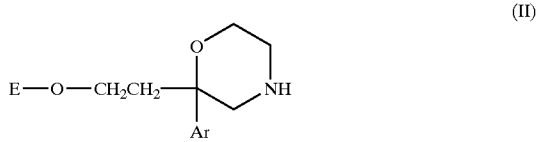

in which Ar is as defined in claim 1, E represents hydrogen or an O-protecting group, is reacted with a functional derivative of an acid of formula:

(III)

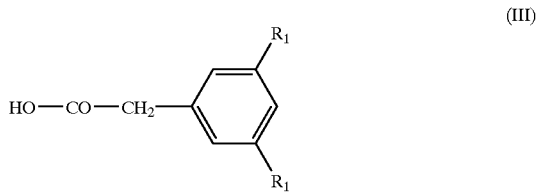

in which $R_1$ is as defined in claim 1, to give a compound of formula:

(IV)

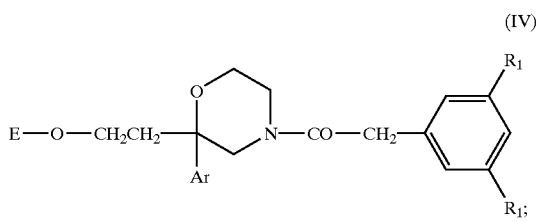

optionally, when E represents a protecting group, it is removed by the action of an acid or a base, to give the alcohol of formula:

(IV, E = H)

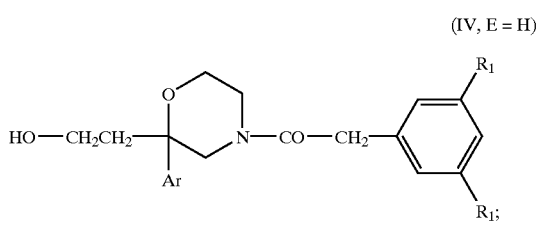

2b) the compound of formula (IV, E=H) thus obtained is oxidized in order to prepare a compound of formula:

(VIII)

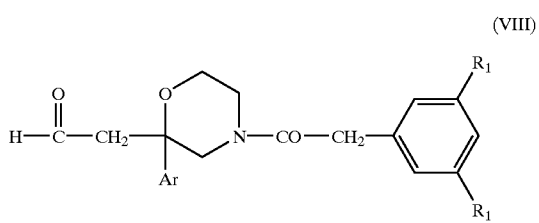

3b) the compound of formula (VIII) is reacted with a compound of formula:

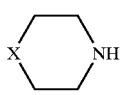

(VII)

in which X is as defined in claim 1, in the presence of an acid, followed by reduction of the intermediate iminium salt formed, by means of a reducing agent;

4b) and, optionally, the compound thus obtained is converted into a salt thereof with an inorganic or organic acid.

22. A compound of formula IV:

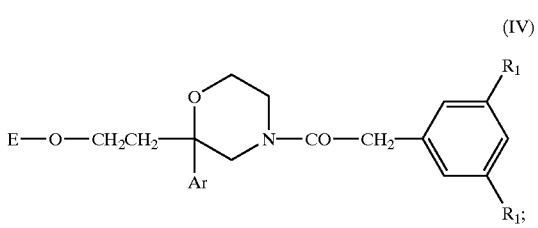

(IV)

in which:
Ar represents a phenyl monosubstituted or disubstituted with a halogen atom or a $(C_1-C_3)$alkyl;
E represents hydrogen or an O-protecting group;
$R_1$ represents a chlorine atom, a bromine atom, a $(C_1-C_3)$ alkyl or a trifluoromethyl;
in enantiomerically pure form or in racemic form.

23. A compound according to claim 22 of formula (IV) in which E represents hydrogen.

24. A compound of formula VI:

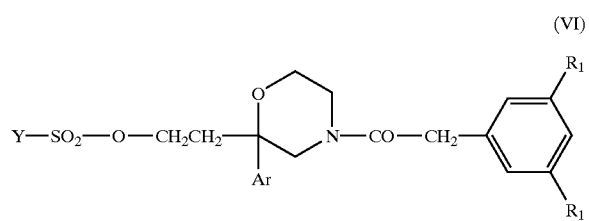

(VI)

in which:
Ar represents a phenyl monosubstituted or disubstituted with a halogen atom or a $(C_1-C_3)$alkyl;
Y represents a methyl, phenyl, tolyl or trifluoromethyl group;
$R_1$ represents a chlorine atom, a bromine atom, a $(C_1-C_3)$ alkyl or a trifluoromethyl,
in enantiomerically pure form or in racemic form.

25. A compound of formula VIII:

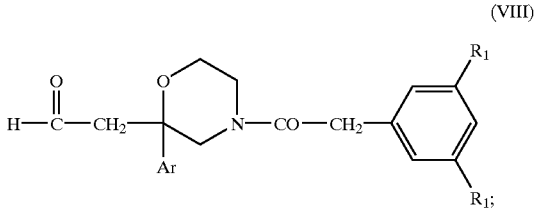

(VIII)

in which:
Ar represents a phenyl monosubstituted or disubstituted with a halogen atom or a $(C_1-C_3)$alkyl;
$R_1$ represents a chlorine atom, a bromine atom, a $(C_1-C_3)$ alkyl or a trifluoromethyl,
in enantiomerically pure form or in racemic form.

26. A pharmaceutical composition comprising, as active principle, a compound according to claim 1.

27. A pharmaceutical composition according to claim 26, containing from 0.1 to 1000 mg of active principle, in unit dosage form, in which the active principle is mixed with at least one pharmaceutical excipient.

28. A compound according to claim 12 in optically pure form.

29. A compound according to claim 13 in optically pure form.

30. A compound according to claim 14 in optically pure form.

31. A pharmaceutical composition containing as active principle a compound according to claim 12.

32. A pharmaceutical composition containing as active principle a compound according to claim 13.

33. A pharmaceutical composition containing as active principle a compound according to claim 14.

34. A method for the treatment of a disease in which substance P and/or the human $NK_1$ receptors are involved which comprises administering to a patient in need of such treatment a therapeutically effective amount of a compound according to claim 1.

35. A method according to claim 34 for the treatment of a respiratory, gastrointestinal, urinary, immune, cardiovascular or central nervous system disease.

36. A method according to claim 34 for the treatment of pain, migraine, inflammation, nausea, vomiting or skin disease.

37. A method according to claim 35 for the treatment of obstructive chronic bronchitis, asthma, urinary incontinence, irritable bowel syndrome, Crohn's disease, ulcerative colitis, depression, anxiety or epilepsy.

* * * * *